United States Patent
Wang et al.

(10) Patent No.: US 9,724,374 B2
(45) Date of Patent: Aug. 8, 2017

(54) CAPSULE CONTAINING TOTAL FLAVONOIDS OF DESMODIUM STYRACIFOLIUM, METHOD FOR PREPARING THE SAME AND USE

(71) Applicant: HUMANWELL HEALTHCARE (GROUP) CO., LTD., Wuhan, Hubei (CN)

(72) Inventors: Xuehai Wang, Hubei (CN); Yong Xu, Hubei (CN); Li'e Li, Hubei (CN); Jie Li, Hubei (CN); Ronghua Tu, Hubei (CN); Gang Chen, Hubei (CN); Rubin Cao, Hubei (CN); Yun Feng, Hubei (CN); Zhongwen Yang, Hubei (CN); Zhaoze Fan, Hubei (CN); Yanping Yu, Hubei (CN); Qiang Xiao, Hubei (CN); Lu Huang, Hubei (CN); Chengbing Yang, Hubei (CN); Tianci Huang, Hubei (CN); Hua Tian, Hubei (CN); Jing Yang, Hubei (CN)

(73) Assignees: HUMANWELL HEALTHCARE (GROUP) CO., LTD., Wuhan, Hubei (CN); WUHAN OPTICS VALLEY HUMANWELL BIO-PHARMACEUTICAL CO., LTD., Wuhan, Hubei (CN); HUBEI BIOLOGICAL MEDICINE INDUSTRIAL TECHNOLOGY INSTITUTE CO., LTD., Wuhan, Hubei (CN); WUHAN CHEMLIGAND BIO-PHARMACEUTICAL CO., LTD., Wuhan, Hubei (CN)

( * ) Notice: Subject to any disclaimer, the term of this patent is extended or adjusted under 35 U.S.C. 154(b) by 0 days.

(21) Appl. No.: 15/101,924

(22) PCT Filed: Jul. 15, 2014

(86) PCT No.: PCT/CN2014/082224
§ 371 (c)(1),
(2) Date: Jun. 5, 2016

(87) PCT Pub. No.: WO2015/081701
PCT Pub. Date: Jun. 11, 2015

(65) Prior Publication Data
US 2016/0296579 A1    Oct. 13, 2016

(30) Foreign Application Priority Data
Dec. 5, 2013   (CN) .......................... 2013 1 0643107

(51) Int. Cl.
| A61K 36/00 | (2006.01) |
| A61K 36/48 | (2006.01) |
| A61K 9/48 | (2006.01) |
| A61K 9/16 | (2006.01) |

(52) U.S. Cl.
CPC ............ *A61K 36/48* (2013.01); *A61K 9/1623* (2013.01); *A61K 9/1635* (2013.01); *A61K 9/1652* (2013.01); *A61K 9/1682* (2013.01); *A61K 9/4833* (2013.01); *A61K 9/4858* (2013.01); *A61K 9/4866* (2013.01); *A61K 9/4875* (2013.01); *A61K 2236/33* (2013.01); *A61K 2236/53* (2013.01)

(58) Field of Classification Search
None
See application file for complete search history.

(56) References Cited

FOREIGN PATENT DOCUMENTS

| CN | 102772441 A | * | 11/2012 |
| JP | 61200921 A | * | 9/1986 |
| JP | 361200921 A | * | 9/1986 |
| JP | 01301688 A | * | 12/1989 |
| JP | 01305080 A | * | 12/1989 |

* cited by examiner

*Primary Examiner* — Qiuwen Mi
(74) *Attorney, Agent, or Firm* — Kile Park Reed & Houtteman LLC

(57) ABSTRACT

A capsule containing total flavonoids of *Desmodium styracifolium*, a method for preparing the same and a use of the capsule containing total flavonoids of *Desmodium styracifolium* are provided. Specifically, the capsule includes total flavonoids of *Desmodium Styracifolium* provided in a form of alcohol extract of *Desmodium Styracifolium* and a pharmaceutically acceptable excipient.

9 Claims, 1 Drawing Sheet

CAPSULE CONTAINING TOTAL FLAVONOIDS OF DESMODIUM STYRACIFOLIUM, METHOD FOR PREPARING THE SAME AND USE

CROSS-REFERENCE TO RELATED APPLICATION

The application is the U.S. national phase of PCT Application No. PCT/CN2014/082224 filed on Jul. 15, 2014, which claims a priority to and benefits of Chinese Patent Applications No. 201310643107.3, filed with the State Intellectual Property Office of P. R. China on Dec. 5, 2013, the entire contents of which are incorporated herein by reference

FIELD

The present disclosure relates to the field of traditional Chinese medicine, in particularly to a capsule containing total flavonoids of *Desmodium styracifolium*, a method for preparing the same and use of the capsule containing total flavonoids of *Desmodium styracifolium* in preparation of a medicament for treating urinary stone.

BACKGROUND

*Desmodium Styracifolium* is a dried overground part of leguminous plants, *Desmodium styracifolium* (Osb.) Merr., as a traditional Chinese medicine recorded in Part I of *Chinese Pharmacopoeia* (2010 edition) having efficacy in disinhibiting dampness-abating jaundice and disinhibiting urine and freeing strangury. A prescription preparation of stranguria-treating and calculus-removing tablet containing *Desmodium Styracifolium* as its essential ingredient, also recorded in *Chinese Pharmacopoeia*, can be used to treat bladder dampness-heat, stone strangury with roughness and pain in the urethra, lithangiuria and urinary infection belonging to dampness and heat in liver, gallbladder and urinary bladder. However, the raw material of the stranguria-treating and calculus-removing tablet is a crude extract of the *Desmodium Styracifolium* which is prepared by a traditional water-extraction and alcohol-precipitation extraction method, and this tablet also has a plurality of drawbacks, such as unclear effective components in Chinese herb, overdose in clinic (6 times a day, three pills one time, sugar-coated tablets or film-coated tablets, each pill containing 0.12 g dry extract) and inadequate standard in quality control. The stone discharging agent, such as potassium citrate, thiazide diuretic, magnesium agent, and acetyl cysteine, which is often used in clinic to treating the lithangiuria, with an non-ideal efficacy and significant toxicity and side effect. Chinese patent medicine, such as "Mi Shi Tong", lithagogue infusion, and stranguria-treating and calculus-removing tablets, is commonly used medicaments with exact effect. However, similar with the stranguria-treating and calculus-removing tablets, all these traditional Chinese medicines still exist such problems, such as original pharmaceutical process, difficulties in quality control, inaccurate quantitative detection method, and overdose, that there is a relative great distance as compared with international standards and does not meet the requirements of modern clinical medicine, in addition, the total flavonoids of *Desmodium Styracifolium* is a water-insoluble medicament.

Therefore, it needs to research and develop new traditional Chinese medicines related to total flavonoids of *Desmodium Styracifolium* with safety and efficacy, controllable quality, and high dissolution rate. Current research on formulations related to total flavonoids of *Desmodium Styracifolium* still needs to be strengthened. It is very necessary to provide an oral solid formulation of the total flavonoids of *Desmodium Styracifolium* with a superior therapeutic effect than that of the existing medicaments, stable and controllable quality for clinic, better adsorption in vivo, safety and efficacy, and economic.

SUMMARY

Embodiments of the present disclosure seek to solve at least one of the problems existing in the related art to at least some extent or provide at least one of commercially available choices. Accordingly, one object of the present disclosure is to provide a capsule containing total flavonoids of *Desmodium styracifolium*, which is of a clear effective material basis, a controllable quality standard, a high dissolution rate, a good quality stability, a remarkable pharmacological effect and a small dosage, and being taken safely and conveniently, and being completely suitable for a large scale of industrial production.

The present disclosure is accomplished by the present inventors based on the following discoveries. The chemical composition of *Desmodium styracifolium* contains flavonoids, alkaloids, phenols, tannins and polysaccharides, in which the total flavonoids are the main effective component. Pharmacology experiments show that the active ingredient (effective component) of *Desmodium styracifolium*, i.e., the total flavonoids of *Desmodium styracifolium*, has significant pharmacological functions of dissolving stone, discharging stone and reducing the formation of stones. In addition, the total flavonoid of *Desmodium Styracifolium* is almost insoluble in water as the physical and chemical properties of its active pharmaceutical ingredients (APIs), but its extractum or powders is prone to sticky (viscosity increases and easy to agglomerate). Therefore, the total flavonoid of *Desmodium Styracifolium* will has a very low dissolution rate if it is formulated into common pharmaceutical formulations. Thus, granulating effect is very poor and granulation almost cannot be carried out using conventional manufacturing processes, which easily leads to the total flavonoid of *Desmodium Styracifolium* thus obtained having a plurality of drawbacks, such as slow dissolution, unstable product quality, low bioavailability, and low clinical efficacy. Additionally, the adsorption of medicaments is based on its dissolution, its bioavailability in vivo is relate to the dissolution rate in vitro in a certain degree, therefore, the dissolution rate of a medicament directly plays a role on its adsorption, the dissolution of the medicament in a formulation is a step to control whether the medicament can exert its efficacy. Furthermore, enhancing the dissolution and release of the medicament is most critical to improve the adsorption rate of oral formulations in the human body, which will increase the maximum plasma concentration of the active ingredient after 3 hours from oral administration.

In a first aspect of the present disclosure, total flavonoids of *Desmodium styracifolium* is provided in embodiments of the present disclosure. According to embodiments of the present disclosure, the total flavonoids of *Desmodium styracifolium* is an alcohol extract of *Desmodium Styracifolium*. In the product of the alcohol extract of *Desmodium Styracifolium*, a content of the total flavonoids of *Desmodium styracifolium* is between 50% and 80% (by the extract after dried, %), in which a content of schaftosides is between 3.0% and 12.0% (by the extract after dried, %).

According to embodiments of the present disclosure, the total flavonoids of *Desmodium styracifolium* are prepared by the following steps: extracting a raw material of *Desmodium Styracifolium* with alcohols, so as to obtain an extracting solution of *Desmodium Styracifolium*; and purifying the extracting solution of *Desmodium Styracifolium*, so as to obtain the alcohol extract of *Desmodium Styracifolium*.

According to some embodiments of the present disclosure, the step of extracting the raw material of *Desmodium Styracifolium* with alcohols further includes: heating and refluxing the raw material of *Desmodium Styracifolium*, for 1 to 3 times with 1 to 3 hours for each time, with ethanol having the concentration ranging from 50% to 95% and the weight ranging from 8 to 14 times than that of *Desmodium Styracifolium* for extraction and mixing the ethanol extracting solutions, so as to obtain the extracting solution of *Desmodium Styracifolium*. According to a specific embodiment of the present disclosure, the step of purifying the extracting solution of *Desmodium Styracifolium* further includes: concentrating the extracting solution of *Desmodium Styracifolium*, so as to remove ethanol; and subjecting the extracting solution of *Desmodium Styracifolium* to adsorption onto a macroporous resin column, so as to obtain purified total flavonoids of *Desmodium Styracifolium*.

Specifically, according to some embodiments of the present disclosure, a method for preparing total flavonoids of *Desmodium Styracifolium* may include steps of:

a. weighing a raw material of *Desmodium Styracifolium*, adding ethanol having a concentration ranging from 50% to 95% and a weight ranging from 8 to 14 times than that of the raw material, heating and refluxing at a temperature of 50° C. to 60° C. for 1 to 3 times with 1 to 3 hours for each time for extraction, so as to obtain an alcohol extracting solution of *Desmodium Styracifolium* followed by mixing;

b. concentrating the alcohol extracting solution to be of a volume ranging from 2 to 8 times than the weight of the raw material followed by still standing and filtration, to obtain filtrate;

c. subjecting the filtrate to adsorption onto an AB-8 macroporous resin column at a flow rate ranging from 1 to 3 column bed volumes per hour, eluting and purifying with water having a volume ranging from 8 to 12 times than the weight of filled resin, and eluting with ethanol having a concentration ranging from 40% to 95% and a volume ranging from 6 to 10 column bed volumes at a flow rate ranging from 2 to 4 column bed volumes per hour, to obtain an eluted solution;

d. recycling ethanol from the eluted solution, and concentrating the eluted solution into a concentrated solution with a relative density ranging from 1.10 to 1.30, to obtain the total flavonoids extract of *Desmodium Styracifolium* after drying and smashing the concentrated solution, in which a content of the total flavonoids of *Desmodium styracifolium* is between 50% and 80% and a content of schaftosides is between 3.0% and 12.0%, collecting the extract after dried, followed by sealing, weighting and keeping in a dry place.

An ethanol concentration used herein refers to a volume fraction (V/V) of the ethanol per 100 mL of ethanol-water solution.

Specifically, according to some embodiments of the present disclosure, a method for preparing total flavonoids extract of *Desmodium Styracifolium* may include steps of:

a. weighing a raw material of *Desmodium Styracifolium*, adding ethanol having a concentration of 80% and a weight of 12 times than that of the raw material, heating and refluxing at a temperature of 55° C. for 2 hours for first extraction, adding ethanol having a concentration of 80% and a weight of 10 times than that of the raw material, heating and refluxing at a temperature of 55° C. for 1.5 hours for second extraction, so as to obtain an alcohol extracting solution of *Desmodium Styracifolium* followed by mixing;

b. concentrating the alcohol extracting solution to be of a volume 5 times than the weight of the raw material followed by still standing and filtration, to obtain filtrate;

c. subjecting the filtrate to adsorption onto an AB-8 macroporous resin column at a flow rate of 2 column bed volumes per hour, eluting and purifying with water having a volume of 10 times than the weight of filled resin, and eluting with ethanol having a concentration of 60% and a volume of 8 column bed volumes at a flow rate of 2 column bed volumes per hour, to obtain an eluted solution;

d. recycling ethanol from the eluted solution, and concentrating the eluted solution into a concentrated solution with a relative density of 1.22, to obtain the total flavonoids extract of *Desmodium Styracifolium* after drying under reduced pressure at 75° C. and smashing.

Specifically, according to some embodiments of the present disclosure, the preparation process and the technology parameters for extracting the total flavonoids of *Desmodium Styracifolium* are investigated and studied in detail, resulting in a preferable condition, which is verified in a pilot test and successfully transited into industrial production.

In embodiments of the present disclosure, contents of effective components and substances of a medicament of *Desmodium styracifolium* are increased. In the alcohol extract of *Desmodium Styracifolium*, a content of the total flavonoids of *Desmodium styracifolium* is between 50% and 80% (by the extract after dried, %), in which a content of schaftosides is between 3.0% and 12.0% (by the extract after dried, %).

According to a second aspect of the present disclosure, a capsule containing total flavonoids of *Desmodium Styracifolium* is provided in embodiments of the present disclosure. According to embodiments of the present disclosure, the capsule includes total flavonoids of *Desmodium Styracifolium* as an active ingredient, provided in a form of alcohol extract of *Desmodium Styracifolium*. According to embodiments of the present disclosure, the alcohol extract of *Desmodium Styracifolium* is obtained by the following steps: heating and refluxing a raw material of *Desmodium Styracifolium* with ethanol, so as to obtain an extracting solution of *Desmodium Styracifolium*, the ethanol being of a concentration ranging from 50% to 95% and a weight ranging from 8 to 14 times than that of the raw material of *Desmodium styracifolium*; concentrating the extracting solution of *Desmodium Styracifolium*, so as to remove ethanol; and subjecting the extracting solution of *Desmodium Styracifolium* after concentrated to adsorption onto a macroporous resin column, so as to obtain the alcohol extract of *Desmodium Styracifolium*. According to embodiments of the present disclosure, the extracting solution of *Desmodium Styracifolium* is obtained by: heating and refluxing the raw material of *Desmodium Styracifolium*, for 1 to 3 times with 1 to 3 hours for each time, with ethanol having the concentration ranging from 50% to 95% and the weight ranging from 8 to 14 times than that of *Desmodium Styracifolium* for extraction, and mixing the ethanol extracting solutions. The present inventors have surprisingly found that the capsule containing total flavonoids of *Desmodium Styracifolium* prepared according to embodiments of the present disclosure is of a high dissolution rate, a remarkable clinical effect, a mild side effect and a good therapeutically effect for urinary stone diseases, in particularly for renal pelvic stones and ureteral stones. The therapeutically effect of the capsule is better than that of stranguria-treating and calculus-removing tablets. Moreover, the effective components and contents of the capsule containing total flavonoids of *Desmodium Styracifolium* are specific, and the quality stability is controllable. The medicament loading capacity of the formulation is large and the dosage is low, resulting in a better absorption in vivo. It is easy to administrate and use the capsule and the price of the capsule is cheap and affordable.

Specifically, according to embodiments of the present disclosure, the capsule containing total flavonoids of *Desmodium Styracifolium* may include: the total flavonoids of *Desmodium Styracifolium* and a pharmaceutically acceptable excipient. The total flavonoids of *Desmodium Styracifolium* is provided in a form of alcohol extract of *Desmodium Styracifolium*, which is prepared by the method for preparing total flavonoids of *Desmodium Styracifolium* according to embodiments of the present disclosure.

According to specific embodiment of the present disclosure, in the capsule containing total flavonoids of *Desmodium Styracifolium* of the present disclosure, the pharmaceutically acceptable excipient may include a filling agent and an adhesion agent.

According to some embodiments of the present disclosure, in the capsule containing total flavonoids of *Desmodium Styracifolium* of the present disclosure, the filling agent is at least one selected from corn starch, dextrin, lactose, pregelatinized starch, saccharose, microcrystalline cellulose, mannitol, sorbitol, xylitol, calcium hydrophosphate and calcium carbonate. Preferably, the filling agent is at least one of xylitol, microcrystalline cellulose and lactose.

According to some embodiments of the present disclosure, the adhesion agent is at least one selected from starch paste, hydroxypropyl methylcellulose, microcrystalline cellulose, povidone $K_{30}$, povidone $K_{25}$, polyethylene glycol 6000, methylcellulose and ethanol. Preferably, the adhesion agent is at least one selected from polyethylene glycol 6000, povidone $K_{30}$, hydroxypropyl methylcellulose and microcrystalline cellulose.

According to some embodiments of the present disclosure, in the capsule containing total flavonoids of *Desmodium Styracifolium* of the present disclosure, the pharmaceutically acceptable excipient further includes a wetting agent, a disintegrating agent and a lubricating agent.

According to some embodiments of the present disclosure, the wetting agent is at least one selected from water and ethanol.

According to some embodiments of the present disclosure, the disintegrating agent is at least one selected from sodium carboxymethyl starch, low-substituted hydroxypropyl cellulose, cross-linked povidone, dry starch, cross-linked sodium carboxymethyl cellulose and calcium carboxymethyl cellulose. Preferably, the disintegrating agent is at least one selected from cross-linked sodium carboxymethyl cellulose, cross-linked povidone and calcium carboxymethyl cellulose.

According to some embodiments of the present disclosure, the lubricating agent is at least one selected from magnesium stearate, talc, aerosil, magnesium dodecyl sulfate, sodium dodecyl sulfate, sodium benzoate and sodium stearyl fumarate. Preferably, the lubricating agent is at least one of magnesium stearate, aerosil, and sodium stearyl fumarate.

According to embodiments of the present disclosure, the capsule containing total flavonoids of *Desmodium Styracifolium* of the present disclosure includes 33 to 400 weight parts of the total flavonoids of *Desmodium Styracifolium*, 30 to 120 weight parts of the filling agent, 0.1 to 10 weight parts of the adhesion agent, 1 to 80 weight parts of the disintegrating agent, 1 to 10 weight parts of the lubricating agent, and 80 to 210 weight parts of the wetting agent.

According to a specific embodiment of the present disclosure, the capsule containing total flavonoids of *Desmodium Styracifolium* of the present disclosure includes 33 weight parts of the total flavonoids of *Desmodium Styracifolium*, 66 weight parts of microcrystalline cellulose, 66 weight parts of lactose, 1 weight part of povidone $K_{30}$, 10 weight parts of cross-linked sodium carboxymethyl cellulose, 1 weight part of sodium stearyl fumarate, and 120 weight parts of water.

According to a specific embodiment of the present disclosure, the capsule containing total flavonoids of *Desmodium Styracifolium* of the present disclosure includes 33 weight parts of the total flavonoids of *Desmodium Styracifolium*, 33 weight parts of microcrystalline cellulose, 33 weight parts of lactose, 60 weight parts of cross-linked povidone, 5 weight parts of polyethylene glycol 6000, 5 weight parts of sodium stearyl fumarate, and 120 weight parts of water.

According to a specific embodiment of the present disclosure, the capsule containing total flavonoids of *Desmodium Styracifolium* of the present disclosure includes 50 weight parts of the total flavonoids of *Desmodium Styracifolium*, 50 weight parts of microcrystalline cellulose, 50 weight parts of lactose, 2 weight parts of polyethylene glycol 6000, 2 weight parts of magnesium stearate, 120 weight parts of ethanol, and 40 weight parts of water.

According to a specific embodiment of the present disclosure, the capsule containing total flavonoids of *Desmodium Styracifolium* of the present disclosure includes 66.5 weight parts of the total flavonoids of *Desmodium Styracifolium*, 40 weight parts of microcrystalline cellulose, 40 weight parts of cross-linked sodium carboxymethyl cellulose, 30 weight parts of cross-linked povidone, 10 weight parts of polyethylene glycol 6000, 5 weight parts of magnesium stearate, and 200 weight parts of water.

According to a specific embodiment of the present disclosure, the capsule containing total flavonoids of *Desmodium Styracifolium* of the present disclosure includes 66.5 weight parts of the total flavonoids of *Desmodium Styracifolium*, 50 weight parts of microcrystalline cellulose, 50 weight parts of lactose, 30 weight parts of calcium carboxymethyl cellulose, 2 weight parts of povidone $K_{30}$, 5 weight parts of magnesium stearate, and 180 weight parts of water.

According to a specific embodiment of the present disclosure, the capsule containing total flavonoids of *Desmodium Styracifolium* of the present disclosure includes 80 weight parts of the total flavonoids of *Desmodium Styracifolium*, 35 weight parts of microcrystalline cellulose, 30 weight parts of lactose, 0.1 weight parts of povidone $K_{30}$, 5 weight parts of magnesium stearate, and 80 weight parts of water.

According to a specific embodiment of the present disclosure, the capsule containing total flavonoids of *Desmodium Styracifolium* of the present disclosure includes 100 weight parts of the total flavonoids of *Desmodium Styracifolium*, 60 weight parts of lactose, 35 weight parts of cross-linked sodium carboxymethyl cellulose, 0.1 weight parts of hydroxypropyl methylcellulose, 2 weight parts of aerosol, 100 weight parts of ethanol, and 10 weight parts of water.

According to a specific embodiment of the present disclosure, the capsule containing total flavonoids of *Desmodium Styracifolium* of the present disclosure includes 100 weight parts of the total flavonoids of *Desmodium Styraci-*

*folium,* 40 weight parts of microcrystalline cellulose, 20 weight parts of cross-linked sodium carboxymethyl cellulose, 40 weight parts of cross-linked povidone, 10 weight parts of polyethylene glycol 6000, 10 weight parts of magnesium stearate, and 210 weight parts of water.

According to a specific embodiment of the present disclosure, the capsule containing total flavonoids of *Desmodium Styracifolium* of the present disclosure includes 120 weight parts of the total flavonoids of *Desmodium Styracifolium,* 40 weight parts of microcrystalline cellulose, 40 weight parts of lactose, 2 weight parts of polyethylene glycol 6000, 2 weight parts of magnesium stearate, and 120 weight parts of water.

According to a specific embodiment of the present disclosure, the capsule containing total flavonoids of *Desmodium Styracifolium* of the present disclosure includes 120 weight parts of the total flavonoids of *Desmodium Styracifolium,* 120 weight parts of lactose, 1 weight part of hydroxypropyl methylcellulose, 1 weight part of magnesium stearate, 100 weight parts of ethanol, and 20 weight parts of water.

According to a specific embodiment of the present disclosure, the capsule containing total flavonoids of *Desmodium Styracifolium* of the present disclosure includes 120 weight parts of the total flavonoids of *Desmodium Styracifolium,* 40 weight parts of microcrystalline cellulose, 40 weight parts of lactose, 1 weight part of polyethylene glycol 6000, 1 weight part of povidone $K_{30}$, 2 weight parts of aerosol, 96 weight parts of ethanol, and 24 weight parts of water.

According to a specific embodiment of the present disclosure, the capsule containing total flavonoids of *Desmodium Styracifolium* of the present disclosure includes 133 weight parts of the total flavonoids of *Desmodium Styracifolium,* 30 weight parts of microcrystalline cellulose, 37 weight parts of lactose, 1 weight part of povidone $K_{30}$, and 120 weight parts of water.

According to a specific embodiment of the present disclosure, the capsule containing total flavonoids of *Desmodium Styracifolium* of the present disclosure includes 133 weight parts of the total flavonoids of *Desmodium Styracifolium,* 30 weight parts of microcrystalline cellulose, 37 weight parts of lactose, 1 weight part of povidone $K_{30}$, 20 weight parts of cross-linked sodium carboxymethyl cellulose, 1 weight part of aerosol, and 120 weight parts of water.

According to a specific embodiment of the present disclosure, the capsule containing total flavonoids of *Desmodium Styracifolium* of the present disclosure includes 133 weight parts of the total flavonoids of *Desmodium Styracifolium,* 33 weight parts of microcrystalline cellulose, 33 weight parts of lactose, 1 weight part of povidone $K_{30}$, 15 weight parts of cross-linked sodium carboxymethyl cellulose, 1 weight part of aerosol, and 120 weight parts of water.

According to a specific embodiment of the present disclosure, the capsule containing total flavonoids of *Desmodium Styracifolium* of the present disclosure includes 150 weight parts of the total flavonoids of *Desmodium Styracifolium,* 30 weight parts of microcrystalline cellulose, 30 weight parts of lactose, 80 weight parts of cross-linked povidone, 5 weight parts of polyethylene glycol 6000, 5 weight parts of sodium stearyl fumarate, 130 weight parts of ethanol, and 45 weight parts of water.

According to a specific embodiment of the present disclosure, the capsule containing total flavonoids of *Desmodium Styracifolium* of the present disclosure includes 150 weight parts of the total flavonoids of *Desmodium Styracifolium,* 30 weight parts of microcrystalline cellulose, 20 weight parts of lactose, 1.2 weight parts of povidone $K_{30}$, 2 weight parts of aerosol, and 80 weight parts of water.

According to a specific embodiment of the present disclosure, the capsule containing total flavonoids of *Desmodium Styracifolium* of the present disclosure includes 200 weight parts of the total flavonoids of *Desmodium Styracifolium,* 30 weight parts of microcrystalline cellulose, 30 weight parts of lactose, 2 weight parts of povidone $K_{30}$, 2 weight parts of aerosol, and 120 weight parts of water.

According to a specific embodiment of the present disclosure, the capsule containing total flavonoids of *Desmodium Styracifolium* of the present disclosure includes 400 weight parts of the total flavonoids of *Desmodium Styracifolium,* 50 weight parts of microcrystalline cellulose, 50 weight parts of lactose, 2 weight parts of povidone $K_{30}$, 4 weight parts of aerosol, and 200 weight parts of water.

According to a third aspect of the present disclosure, a method for preparing a capsule containing total flavonoids of *Desmodium Styracifolium* is provided in embodiments of the present discloduture. According to embodiments of the present disclosure, the method includes steps of: providing the total flavonoids of *Desmodium Styracifolium* in a form of an alcohol extract of *Desmodium Styracifolium*; and capsulizing the alcohol extract of *Desmodium Styracifolium* with a pharmaceutically acceptable excipient.

The total flavonoids of *Desmodium Styracifolium* is mixed with lactoses to be uniform by the inventor at first through a conventional wet granulation process, then added with an aqueous solution of povidone $K_{30}$ and stirred to be uniform for preparing a soft material, which is subjected to granulating, drying, size stabilizing and capsulizing, thereby obtaining the capsule containing total flavonoids of *Desmodium Styracifolium,* with a content uniformity meeting requirements recorded in Appendix IL, Part 1 of Chinese Pharmacopoeia (2010 edition). Because the total flavonoid extract of *Desmodium Styracifolium* is difficult to be dissolved in water and becomes sticky when encountering water (viscosity is increased), it has been found that the total flavonoids extract of *Desmodium Styracifolium* is hardly to be granulated with poor granulating effect during manually granulation process in lab-scale tests. Although the total flavonoids extract of *Desmodium Styracifolium* can be granulated with improved granulating effects using a granulating machine, a dissolution ration is between 73% and 78% with a relative large difference between batches. Besides, it has been detected that a resulting product is in danger of becoming unqualified during long term storage. The dissolution rate cannot be improved even through screening and optimizing the formula.

Expected advantageous effects have been achieved through continuous experiments and exploration by the present inventors. It has been surprisingly found out that, instead of the conventional wet granulation process, the fluidized bed granulation process allows the total flavonoid extract of *Desmodium Styracifolium* to be granulated with obviously improved granulating effects, for example, the dissolution ration of the capsule containing total flavonoid extract of *Desmodium Styracifolium* is enhanced (e.g., stabilized between 88% to 92%) with less difference between batches as compared with the conventional process. Moreover, such a process effectively guarantees quality products, and improves stability of formulation containing effective components and the dissolution rate of the medicament. In addition, such the process is simple, maneuverable and, completely suitable for a large scale of industry production.

According to some embodiments of the present disclosure, providing the total flavonoids of *Desmodium Styraci-*

*folium* in the form of the alcohol extract of *Desmodium Styracifolium* further includes: extracting a raw material of *Desmodium Styracifolium* with alcohols, so as to obtain an extracting solution of *Desmodium Styracifolium*; and purifying the extracting solution of *Desmodium Styracifolium*, so as to obtain the alcohol extract of *Desmodium Styracifolium*. According to embodiments of the present disclosure, the step of extracting a raw material of *Desmodium Styracifolium* with alcohols further includes: heating and refluxing the raw material of *Desmodium Styracifolium*, for 1 to 3 times with 1 to 3 hours for each time, with ethanol having the concentration ranging from 50% to 95% and the weight ranging from 8 to 14 times than that of *Desmodium Styracifolium* for extraction, and mixing the ethanol extracting solutions, so as to obtain the extracting solution of *Desmodium Styracifolium*. According to a specific embodiment of the present disclosure, the step of purifying the extracting solution of *Desmodium Styracifolium* further includes: concentrating the extracting solution of *Desmodium Styracifolium*, so as to remove ethanol; and subjecting the extracting solution of *Desmodium Styracifolium* to adsorption onto a macroporous resin column, so as to obtain purified total flavonoids of *Desmodium Styracifolium*.

According to some embodiments of the present disclosure, in the method for preparing the capsule containing total flavonoids of *Desmodium Styracifolium* with a fluidized bed granulation process, the pharmaceutically acceptable excipient includes a filling agent and an adhesion agent.

According to some embodiments of the present disclosure, in the method for preparing the capsule containing total flavonoids of *Desmodium Styracifolium* with a fluidized bed granulation process, the pharmaceutically acceptable excipient further includes a wetting agent, a disintegrating agent and a lubricating agent.

According to embodiments of the present disclosure, in the method for preparing the capsule containing total flavonoids of *Desmodium Styracifolium* with a fluidized bed granulation process, capsulizing total flavonoids of *Desmodium Styracifolium* in a capsule may further include: mixing the total flavonoids of *Desmodium Styracifolium* and an acceptable excipient to prepare the capsule with a pharmaceutically acceptable excipient.

According to embodiments of the present disclosure, capsulizing the total flavonoids of *Desmodium Styracifolium* may further include: mixing the total flavonoids of *Desmodium Styracifolium* with the pharmaceutically acceptable excipient, to obtain a mixture; subjecting the mixture to preheating, spraying, drying, cooling, mixing and size stabilizing with a fluidized bed for granulation, to obtain granules; capsulizing the granules to obtain the capsule containing total flavonoids of *Desmodium Styracifolium*.

Specifically, according to an embodiment of the present disclosure, the step of mixing the total flavonoids extract of *Desmodium Styracifolium* with the pharmaceutically acceptable excipient further includes: subjecting the total flavonoids extract of *Desmodium Styracifolium*, the filling agent, the adhesion agent, the disintegrating agent and the lubricating agent in respective formula dosage to sieving at 40 to 120 meshes, respectively; dissolving the adhesion agent in water to obtain a solution of the adhesion agent after stirring for use; preheating the total flavonoids extract of *Desmodium Styracifolium* and the filling agent in respective formula dosage in a fluidized bed; granulating by spraying, with gunjet, the solution of the adhesion agent into the fluidized bed (after adjusted with suitable parameters); drying by adjusting parameters after the granulation; cooling and discharging the granules after dried; mixing with the disintegrating agent and the lubricating agent in a mixer; subjecting to size stabilization; mixing to be uniform, and capsulizing to obtain the capsule containing total flavonoids of *Desmodium Styracifolium*.

Specifically, according to an embodiment of the present disclosure, the step of preparing the capsule containing total flavonoids of *Desmodium Styracifolium* through the fluidized bed granulation process may further include: subjecting the total flavonoids extract of *Desmodium Styracifolium* and the pharmaceutically acceptable excipient in respective formula dosage to sieving at 60 to 100 meshes, respectively; dissolving the adhesion agent in water to obtain a solution of the adhesion agent after stirring for use; preheating the total flavonoids extract of *Desmodium Styracifolium* and the filling agent in respective formula dosage to 35° C. to 55° C. for 5 min to 60 min in a fluidized bed; granulating by spraying, with gunjet under an atomizing pressure ranging from 0.7 bar to 1.0 bar (1 bar=0.1 MPa) and a spraying speed ranging from 15 rpm/min to 25 rpm/min, the solution of the adhesion agent into the fluidized bed (after adjusted with suitable parameters), enabling materials therein to be of a material temperature of 40° C. to 55° C. by adjusting air inlet temperature of 50° C. to 65° C., by which the adhesion agent is completely sprayed within 5 min to 60 min; drying resulting granules in the fluidized bed, enabling materials therein to be of the material temperature of 40° C. to 55° C. by the adjusting air inlet temperature of 60° C. to 70° C., drying for 5 min to 60 min; cooling and discharging the granules after dried, mixing with the disintegrating agent in a mixer, subjecting to size stabilizing by sieving at 40 to 80 meshes, adding the lubricating agent followed by mixing to be uniform, and capsulizing to obtain the capsule containing total flavonoids of *Desmodium Styracifolium*.

According to embodiments of the present disclosure, in the method for preparing the capsule containing total flavonoids of *Desmodium Styracifolium*, the filling agent is preferably at least one selected from xylitol, microcrystalline cellulose and lactose.

According to embodiments of the present disclosure, in the method for preparing the capsule containing total flavonoids of *Desmodium Styracifolium*, the adhesion agent is preferably at least one selected from polyethylene glycol 6000, povidone $K_{30}$ and hydroxypropyl methylcellulose.

According to embodiments of the present disclosure, in the method for preparing the capsule containing total flavonoids of *Desmodium Styracifolium*, the wetting agent is preferably water.

According to embodiments of the present disclosure, in the method for preparing the capsule containing total flavonoids of *Desmodium Styracifolium*, the disintegrating agent is preferably at least one selected from cross-linked sodium carboxymethyl cellulose, cross-linked povidone and calcium carboxymethyl cellulose.

According to embodiments of the present disclosure, in the method for preparing the capsule containing total flavonoids of *Desmodium Styracifolium*, the lubricating agent is preferably at least one selected from magnesium stearate, aerosol and sodium stearyl fumarate.

According to embodiments of the present disclosure, the capsule containing total flavonoids of *Desmodium Styracifolium* is formulated as below: 33 to 400 weight parts of the total flavonoids of *Desmodium Styracifolium*, 30 to 120 weight parts of the filling agent, 0.1 to 10 weight parts of the adhesion agent, 1 to 80 weight parts of the disintegrating agent, 1 to 10 weight parts of the lubricating agent, and 80 to 210 weight parts of the wetting agent.

According to a specific embodiment of the present disclosure, the capsule containing total flavonoids of *Desmodium Styracifolium* is formulated as below: 33 weight parts of the total flavonoids of *Desmodium Styracifolium*, 66 weight parts of microcrystalline cellulose, 66 weight parts of lactose, 1 weight part of povidone $K_{30}$, 10 weight parts of cross-linked sodium carboxymethyl cellulose, 1 weight part of sodium stearyl fumarate, and 120 weight parts of water.

According to a specific embodiment of the present disclosure, the capsule containing total flavonoids of *Desmodium Styracifolium* is formulated as below: 33 weight parts of the total flavonoids of *Desmodium Styracifolium*, 33 weight parts of microcrystalline cellulose, 33 weight parts of lactose, 60 weight parts of cross-linked povidone, 5 weight parts of polyethylene glycol 6000, 5 weight parts of sodium stearyl fumarate, and 120 weight parts of water.

According to a specific embodiment of the present disclosure, the capsule containing total flavonoids of *Desmodium Styracifolium* is formulated as below: 50 weight parts of the total flavonoids of *Desmodium Styracifolium*, 50 weight parts of microcrystalline cellulose, 50 weight parts of lactose, 2 weight parts of polyethylene glycol 6000, 2 weight parts of magnesium stearate, 120 weight parts of ethanol, and 40 weight parts of water.

According to a specific embodiment of the present disclosure, the capsule containing total flavonoids of *Desmodium Styracifolium* is formulated as below: 66.5 weight parts of the total flavonoids of *Desmodium Styracifolium*, 40 weight parts of microcrystalline cellulose, 40 weight parts of cross-linked sodium carboxymethyl cellulose, 30 weight parts of cross-linked povidone, 10 weight parts of polyethylene glycol 6000, 5 weight parts of magnesium stearate, and 200 weight parts of water.

According to a specific embodiment of the present disclosure, the capsule containing total flavonoids of *Desmodium Styracifolium* is formulated as below: 66.5 weight parts of the total flavonoids of *Desmodium Styracifolium*, 50 weight parts of microcrystalline cellulose, 50 weight parts of lactose, 30 weight parts of calcium carboxymethyl cellulose, 2 weight parts of povidone $K_{30}$, 5 weight parts of magnesium stearate, and 180 weight parts of water.

According to a specific embodiment of the present disclosure, the capsule containing total flavonoids of *Desmodium Styracifolium* is formulated as below: 80 weight parts of the total flavonoids of *Desmodium Styracifolium*, 35 weight parts of microcrystalline cellulose, 30 weight parts of lactose, 0.1 weight parts of povidone $K_{30}$, 5 weight parts of magnesium stearate, and 80 weight parts of water.

According to a specific embodiment of the present disclosure, the capsule containing total flavonoids of *Desmodium Styracifolium* is formulated as below: 100 weight parts of the total flavonoids of *Desmodium Styracifolium*, 60 weight parts of lactose, 35 weight parts of cross-linked sodium carboxymethyl cellulose, 0.1 weight parts of hydroxypropyl methylcellulose, 2 weight parts of aerosol, 100 weight parts of ethanol, and 10 weight parts of water.

According to a specific embodiment of the present disclosure, the capsule containing total flavonoids of *Desmodium Styracifolium* is formulated as below: 100 weight parts of the total flavonoids of *Desmodium Styracifolium*, 40 weight parts of microcrystalline cellulose, 20 weight parts of cross-linked sodium carboxymethyl cellulose, 40 weight parts of cross-linked povidone, 10 weight parts of polyethylene glycol 6000, 10 weight parts of magnesium stearate, and 210 weight parts of water.

According to a specific embodiment of the present disclosure, the capsule containing total flavonoids of *Desmodium Styracifolium* is formulated as below: 120 weight parts of the total flavonoids of *Desmodium Styracifolium*, 40 weight parts of microcrystalline cellulose, 40 weight parts of lactose, 2 weight parts of polyethylene glycol 6000, 2 weight parts of magnesium stearate, and 120 weight parts of water.

According to a specific embodiment of the present disclosure, the capsule containing total flavonoids of *Desmodium Styracifolium* is formulated as below: 120 weight parts of the total flavonoids of *Desmodium Styracifolium*, 120 weight parts of lactose, 1 weight part of hydroxypropyl methylcellulose, 1 weight part of magnesium stearate, 100 weight parts of ethanol, and 20 weight parts of water.

According to a specific embodiment of the present disclosure, the capsule containing total flavonoids of *Desmodium Styracifolium* is formulated as below: 120 weight parts of the total flavonoids of *Desmodium Styracifolium*, 40 weight parts of microcrystalline cellulose, 40 weight parts of lactose, 1 weight part of polyethylene glycol 6000, 1 weight part of povidone $K_{30}$, 2 weight parts of aerosol, 96 weight parts of ethanol, and 24 weight parts of water.

According to a specific embodiment of the present disclosure, the capsule containing total flavonoids of *Desmodium Styracifolium* is formulated as below: 133 weight parts of the total flavonoids of *Desmodium Styracifolium*, 30 weight parts of microcrystalline cellulose, 37 weight parts of lactose, 1 weight part of povidone $K_{30}$, and 120 weight parts of water.

According to a specific embodiment of the present disclosure, the capsule containing total flavonoids of *Desmodium Styracifolium* is formulated as below: 133 weight parts of the total flavonoids of *Desmodium Styracifolium*, 30 weight parts of microcrystalline cellulose, 37 weight parts of lactose, 1 weight part of povidone $K_{30}$, 20 weight parts of cross-linked sodium carboxymethyl cellulose, 1 weight part of aerosol, and 120 weight parts of water.

According to a specific embodiment of the present disclosure, the capsule containing total flavonoids of *Desmodium Styracifolium* is formulated as below: 133 weight parts of the total flavonoids of *Desmodium Styracifolium*, 33 weight parts of microcrystalline cellulose, 33 weight parts of lactose, 1 weight part of povidone $K_{30}$, 15 weight parts of cross-linked sodium carboxymethyl cellulose, 1 weight part of aerosol, and 120 weight parts of water.

According to a specific embodiment of the present disclosure, the capsule containing total flavonoids of *Desmodium Styracifolium* is formulated as below: 150 weight parts of the total flavonoids of *Desmodium Styracifolium*, 30 weight parts of microcrystalline cellulose, 30 weight parts of lactose, 80 weight parts of the cross-linked povidone, 5 weight parts of polyethylene glycol 6000, 5 weight parts of sodium stearyl fumarate, 130 weight parts of ethanol, and 45 weight parts of water.

According to a specific embodiment of the present disclosure, the capsule containing total flavonoids of *Desmodium Styracifolium* is formulated as below: 150 weight parts of the total flavonoids of *Desmodium Styracifolium*, 30 weight parts of microcrystalline cellulose, 20 weight parts of lactose, 1.2 weight parts of povidone $K_{30}$, 2 weight parts of aerosol, and 80 weight parts of water.

According to a specific embodiment of the present disclosure, the capsule containing total flavonoids of *Desmodium Styracifolium* is formulated as below: 200 weight parts of the total flavonoids of *Desmodium Styracifolium*, 30 weight parts of microcrystalline cellulose, 30 weight parts of lactose, 2 weight parts of povidone $K_{30}$, 2 weight parts of aerosol, and 120 weight parts of water.

According to a specific embodiment of the present disclosure, the capsule containing total flavonoids of *Desmodium Styracifolium* is formulated as below: 400 weight parts of the total flavonoids of *Desmodium Styracifolium*, 50 weight parts of microcrystalline cellulose, 50 weight parts of lactose, 2 weight parts of povidone $K_{30}$, 4 weight parts of aerosol, and 200 weight parts of water.

Specifically, according to some embodiments of the present disclosure, the method for preparing the capsule containing total flavonoids of *Desmodium Styracifolium* may include steps of:

a. weighing a raw material of *Desmodium Styracifolium*, adding ethanol having a concentration ranging from 50% to 95% and a weight ranging from 8 to 14 times than that of the raw material, heating and refluxing at a temperature of 50° C. to 60° C. for 1 to 3 times with 1 to 3 hours for each time for extraction, so as to obtain an alcohol extracting solution of *Desmodium Styracifolium* followed by mixing; concentrating the alcohol extracting solution to be of a volume ranging from 2 to 8 times than the weight of the raw material followed by still standing and filtration, to obtain filtrate; subjecting the filtrate to adsorption onto an AB-8 macroporous resin column at a flow rate ranging from 1 to 3 column bed volumes per hour, eluting and purifying with water having a volume ranging from 8 to 12 times than the weight of filled resin, and eluting with ethanol having a concentration ranging from 40% to 95% and a volume ranging from 6 to 10 column bed volumes at a flow rate ranging from 2 to 4 column bed volumes per hour, to obtain an eluted solution; recycling ethanol from the eluted solution, and concentrating the eluted solution into a concentrated solution with a relative density ranging from 1.10 to 1.30, to obtain the total flavonoids extract of *Desmodium Styracifolium* after drying and smashing the concentrated solution;

b. subjecting the total flavonoids extract of *Desmodium Styracifolium* and the pharmaceutically acceptable excipient in respective formula dosage to sieving at 60 to 100 meshes, respectively; and dissolving the adhesion agent in water to obtain a solution of the adhesion agent after stirring for use;

c. preheating the total flavonoids extract of *Desmodium Styracifolium* and the filling agent in respective formula dosage to 35° C. to 55° C. for 5 min to 60 min in a fluidized bed; granulating by spraying, with gunjet under an atomizing pressure ranging from 0.7 bar to 1.0 bar (1 bar=0.1 MPa) and a spraying speed ranging from 15 rpm/min to 25 rpm/min, the solution of the adhesion agent into the fluidized bed (after adjusted with suitable parameters), enabling materials therein to be of a material temperature of 40° C. to 55° C. by adjusting air inlet temperature of 50° C. to 65° C., by which the solution of the adhesion agent is completely sprayed within 5 min to 60 min;

d. drying resulting granules in the fluidized bed (adjusted with suitable parameters), enabling materials therein to be of the material temperature of 40° C. to 55° C. by the adjusting air inlet temperature of 60° C. to 70° C., for 5 min to 60 min;

e. cooling and discharging the granules after dried, mixing with the disintegrating agent in a mixer, subjecting to size stabilizing by sieving at 40 to 80 meshes, adding the lubricating agent followed by mixing to be uniform, and capsulizing to obtain the capsule containing total flavonoids of *Desmodium Styracifolium*.

Specifically, according to one embodiment of the present disclosure, the method for preparing the capsule containing total flavonoids of *Desmodium Styracifolium* may include steps of:

a. weighing a raw material of *Desmodium Styracifolium*, adding ethanol having a concentration of 80% and a weight of 12 times than that of the raw material, heating and refluxing at a temperature of 55° C. for 2 hours for first extraction, adding ethanol having a concentration of 80% and a weight of 10 times than that of the raw material, heating and refluxing at a temperature of 55° C. for 1.5 hours for second extraction, so as to obtain an alcohol extracting solution of *Desmodium Styracifolium* followed by mixing; concentrating the alcohol extracting solution to be of a volume 5 times than the weight of the raw material followed by still standing and filtration, to obtain filtrate; subjecting the filtrate to adsorption onto an AB-8 macroporous resin column at a flow rate of 2 column bed volumes per hour, eluting and purifying with water having a volume of 10 times than the weight of filled resin, and eluting with ethanol having a concentration of 60% and a volume of 8 column bed volumes at a flow rate of 2 column bed volumes per hour, to obtain an eluted solution; recycling ethanol from the eluted solution, and concentrating the eluted solution into a concentrated solution with a relative density of 1.22, to obtain the total flavonoids extract of *Desmodium Styracifolium* after drying under reduced pressure at 75° C. and smashing;

b. subjecting the total flavonoids extract of *Desmodium Styracifolium*, microcrystalline cellulose, lactose, povidone $K_{30}$ and cross-linked sodium carboxymethyl cellulose in respective formula dosage to sieving at 80 meshes, respectively; dissolving the adhesion agent of povidone $K_{30}$ in water to obtain a solution of the adhesion agent after stirring for use;

c. preheating the total flavonoids extract of *Desmodium Styracifolium*, microcrystalline cellulose, and lactose in respective formula dosage to 45° C. for 20 min in a fluidized bed; granulating by spraying, with gunjet under an atomizing pressure of 0.9 bar and a spraying speed of 20 rpm/min, the solution of the adhesion agent into the fluidized bed (after adjusted with suitable parameters), enabling materials therein to be of a material temperature of 45° C. by adjusting the air inlet temperature of 55° C., by which the solution of the adhesion agent is completely sprayed within 15 min;

d. drying resulting granules in the fluidized bed, enabling materials therein to be of the material temperature of 45° C. by the adjusting air inlet temperature of 65° C., for 10 min;

e. cooling and discharging the granules after dried, mixing with cross-linked sodium carboxymethyl cellulose in a mixer, subjecting to size stabilizing by sieving at 60 meshes, adding aerosil followed by mixing to be uniform, and capsulizing to obtain the capsule containing total flavonoids of *Desmodium Styracifolium*.

Specifically, according to another embodiment of the present disclosure, the method for preparing the capsule containing total flavonoids of *Desmodium Styracifolium* may include steps of:

a. weighing a raw material of *Desmodium Styracifolium*, adding ethanol having a concentration of 80% and a weight of 12 times than that of the raw material, heating and refluxing at a temperature of 55° C., extracting for 2 hours for first extraction, adding ethanol having a concentration of 80% and a weight of 10 times than that of the raw material, heating and refluxing at a temperature of 55° C., extracting for 1.5 hours for second extraction, so as to obtain an alcohol extracting solution of *Desmodium Styracifolium* followed by mixing; concentrating the alcohol extracting solution to be of a volume 5 times than the weight of the raw material followed by still standing and filtration, to obtain filtrate; subjecting the filtrate to adsorption onto an AB-8 macroporous resin column at a flow rate of 2 column bed volumes per hour, eluting and purifying with water having a volume of 10 times than the weight of filled resin, and eluting with ethanol having a concentration of 60% and a volume of 8 column bed volumes at a flow rate of 2 column bed volumes per hour, to obtain an eluted solution; recycling ethanol from the eluted solution, and concentrating the eluted solution into a concentrated solution with a relative density of 1.22, to obtain the total flavonoids extract of *Desmodium Styracifolium* after drying under reduced pressure at 75° C. and smashing the concentrated solution;

b. subjecting the total flavonoids extract of *Desmodium Styracifolium*, microcrystalline cellulose, lactose and povidone $K_{30}$ in respective formula dosage to sieving at 80 meshes, respectively; dissolving the adhesion agent of povidone $K_{30}$ in water to obtain a solution of the adhesion agent after stirring for use;

c. preheating the total flavonoids extract of *Desmodium Styracifolium*, microcrystalline cellulose and lactose in respective formula dosage to 45° C. for 20 min in a fluidized bed; granulating by spraying, with gunjet under an atomizing pressure of 0.9 bar and a spraying speed of 20 rpm/min, the solution of the adhesion agent into the fluidized bed (after adjusted with suitable parameters), enabling materials therein to be of a material temperature of 45° C. by adjusting air inlet temperature of 55° C., by which the solution of the adhesion agent is completely sprayed within 15 min;

d. drying resulting granules in the fluidized bed, enabling materials therein to be of the material temperature of 45° C. by the adjusting air inlet temperature of 65° C., for 10 min;

e. cooling and discharging the granules after dried, subjecting to size stabilizing by sieving at 60 meshes, and capsulizing to obtain the capsule containing total flavonoids of *Desmodium Styracifolium*.

Three batches of capsules containing total flavonoids of *Desmodium Styracifolium* are prepared by the present inventor by the method according to embodiments of the present disclosure, which are subjected to a preliminary investigation on stability. According to the requirement of "the Guiding Principle of Pharmaceutical stability Test" (Appendix XIXC, part 2 of *Chinese Pharmacopoeia* (2010 edition)), influencing factor test, acceleration test and long term test are performed, respectively, and the results show that the capsules containing total flavonoids of *Desmodium Styracifolium* are stable under lighting condition. A variety of physical chemistry indexes of the capsule have no significant change at a high temperature of 60° C., a relative humidity of 75% for 10 days, under acceleration condition of a temperature of 40° C. for 6 months, or under a long term condition for 6 months.

According to a fourth aspect of the present disclosure, a capsule containing total flavonoids of *Desmodium Styracifolium* is provided. According to embodiments of the present disclosure, the capsule is prepared by the method for preparing the total flavonoids of *Desmodium Styracifolium* described above.

According to a fifth aspect of the present disclosure, use of the capsule containing total flavonoids of *Desmodium Styracifolium* in medicine is provided. According to embodiments of the present disclosure, the capsule containing total flavonoids of *Desmodium Styracifolium* prepared by embodiments of the present disclosure may be used in preparation of a clinical therapeutic medicament for scavenging dampness and heat or expelling stone through diuresis (stagnation of dampness-heat).

Based on general pharmacological experiments performed according to embodiments of the present disclosure, after administration of the total flavonoids of *Desmodium Styracifolium*, there is no obvious change in behaviour, reaction, action, emotion and gait of the animal, and there is no effect on spontaneous activity of the animal, on excitability to central nervous system of the animal or on gastrointestinal movement of the mouse. The results from pharmacological experiments according to embodiments of the present disclosure show that: the total flavonoids of *Desmodium Styracifolium* may obviously inhibit an amount of calcium oxalate crystalline polymer in kidney, and decrease formation rate of kidney stone and reduce content of creatinine and uric acid, thus improving the kidney function of rat. The total flavonoids of *Desmodium Styracifolium* may have functions in dissolving stones and reducing formation of new stones, and may also have diuretic effect. Moreover, the total flavonoids of *Desmodium Styracifolium* may reduce welling degree and swelling rate caused by injecting egg albumen to toes of rats, which indicates that the total flavonoids of *Desmodium Styracifolium* may have certain anti-inflammatory effect and have obvious inhibiting effect on proliferation of granulation tissue.

According to embodiments of the present disclosure, acute toxicity tests were performed to animals for evaluating safety of the total flavonoids of *Desmodium Styracifolium*. Mice were administrated with the capsule containing total flavonoids of *Desmodium Styracifolium* by gavage for acute toxicity observation, corresponding results show that the total flavonoids of *Desmodium Styracifolium* is a substantially nontoxic to the mice. Rats were administrated with the capsule containing total flavonoids of *Desmodium Styracifolium* by gavage for acute toxicity observation, corresponding results show that there is no server acute toxicity for the rats administrated with the total flavonoids of *Desmodium Styracifolium*. In long term toxicity tests, the total flavonoids of *Desmodium Styracifolium* have also been proven to be safe for animals.

From random, double-blind, multi-dosage parallel-controlled and multi-centered clinical trials (approval document of medicament clinical trial: 2007L04844) for evaluating efficacy and safety of the capsule containing total flavonoids of *Desmodium Styracifolium* in treating urinary stone (stagnation of dampness-heat), it has been turned out that the efficacy of the capsule containing total flavonoids of *Desmodium Styracifolium* in treating urinary stone (stagnation of dampness-heat) is 95.65% (each capsule containing total flavonoids extract of *Desmodium Styracifolium* for the clinical trials contains 133 mg of the total flavonoids extract of *Desmodium Styracifolium*, orally administrated, 3 times per day, 3 capsules each time, for 4 weeks as administration scheme).

As compared with the related art, the technical solution of the present disclosure has advantages as described below.

1. As for traditional Chinese medicament, there exist problems such as a raw process and a large dosage, that is the traditional Chinese medicament still has defects such as a raw preparation process, an unclear active ingredients, a barely controlled quality, an inaccuracy quantitative analysis, a large dosage and a difficulty in administration, so that the traditional Chinese medicament is not suitable for modern life and is not qualified in modern clinical trial. According to embodiments of the present disclosure, there is provided the preparing process for extracting and separating insoluble total flavonoids of *Desmodium Styracifolium* (by means of screening the total flavonoids of *Desmodium Styracifolium* as active ingredient from the raw material and macroporous resin technique) and a granulating process for preparing Chinese medicament with the fluidized bed, such that the capsule containing total flavonoids of *Desmodium Styracifolium* is developed as a modern and new Chinese medicament capable of effectively treating urinary stones with high dissolution rate and quality stability.

2. According to embodiments of the present disclosure, in the process for extracting and purifying the raw material, ethanol is used as an extraction solvent for extracting the raw material of *Desmodium Styracifolium*, and the extracting solution is purified by a macroporous adsorption resin to obtain the active ingredient of *Desmodium Styracifolium*, i.e., the total flavonoids of *Desmodium Styracifolium*. As compared with a water-extraction and alcohol-precipitation method for extracting, the active ingredient basis of the extract by such a process is clear and the quality standard is controllable, thus decreasing the dosage for clinical administration and reducing clinical side effects.

3. As compared with a process of ethanol extracting and macroporous resin purifying in the related art, ethanol is recycled from the extracting solution in embodiments of the present disclosure, so that the extracting solution is concentrated to be of a certain volume (5 times of the weight of the raw material) as a consequence, which can be directed purified by the macroporous resin without special concentrating and drying for into extractum, thus saving time for preparation. Besides, after purified by the macroporous resin, the active ingredient with a high content is eluted even using ethanol with the same concentration, which is a simple process and has a good operability as compared with gradient dilution using ethanol with different concentrations. Thirdly, the total flavonoids of *Desmodium Styracifolium* (i.e., the active ingredient of *Desmodium Styracifolium*) is obtained by recycling ethanol from the eluted solution and directly drying under reduced pressure without any solvent for processing, thus saving consumption in the preparation. In the view of scale production, the above mentioned process for extracting and purifying decreases production costs, shortens production period, which is simple, convenient and practical, thus meeting requirements to modern industry of Chinese medicine.

4. According to embodiments of the present disclosure, the method includes extracting and purifying the active ingredients by means of AB-8 macroporous adsorption resin technique, which is a simple process with low costs as the resin is reusable, thus being suitable for industry production. Moreover, in embodiments of the present disclosure, an optimal condition has been selected by carefully investigating corresponding parameters, which is verified in a pilot test and can be transited into industrial production, thereby increasing the content of the active ingredient. In the total flavonoids extract of *Desmodium Styracifolium*, the total flavonoids of *Desmodium styracifolium* is of a content between 50% and 80%, in which a schaftoside content is between 3.0% and 12.0%.

5. As for the formulation process according to embodiments of the present disclosure, it has been found out that, instead of the conventional wet granulation process, the fluidized bed granulation process allows the total flavonoid extract of *Desmodium Styracifolium* to be granulated with obviously improved granulating effects, for example, the dissolution ration of the capsule containing total flavonoid extract of *Desmodium Styracifolium* is enhanced (e.g., stabilized between 88% to 92%) with less difference between batches as compared with the conventional process. Moreover, such a process effectively guarantees quality products, and improves stability of formulation containing effective components and the dissolution rate of the medicament. In addition, such the process is simple, maneuverable and, completely suitable for a large scale of industry production.

6. As compared with commercially available medicaments with the same use, the capsule containing total flavonoids of *Desmodium Styracifolium* prepared according to embodiments of the present disclosure has a developed production process, a clear active ingredient basis, a controllable quality, a clear and definite clinical indication, a significant pharmacological efficacy, a small dosage, a safe and convenient administration and a mild side effect, so that the capsule of the present disclosure has the advantage of being suitable to technique and quality standard of the modern manufacturing industry. The capsule is mainly used to treat: dampness-heat, diuresis and expelling stone, a dribbling pain caused by stagnation of dampness-heat and urinary stone.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Figure 1:
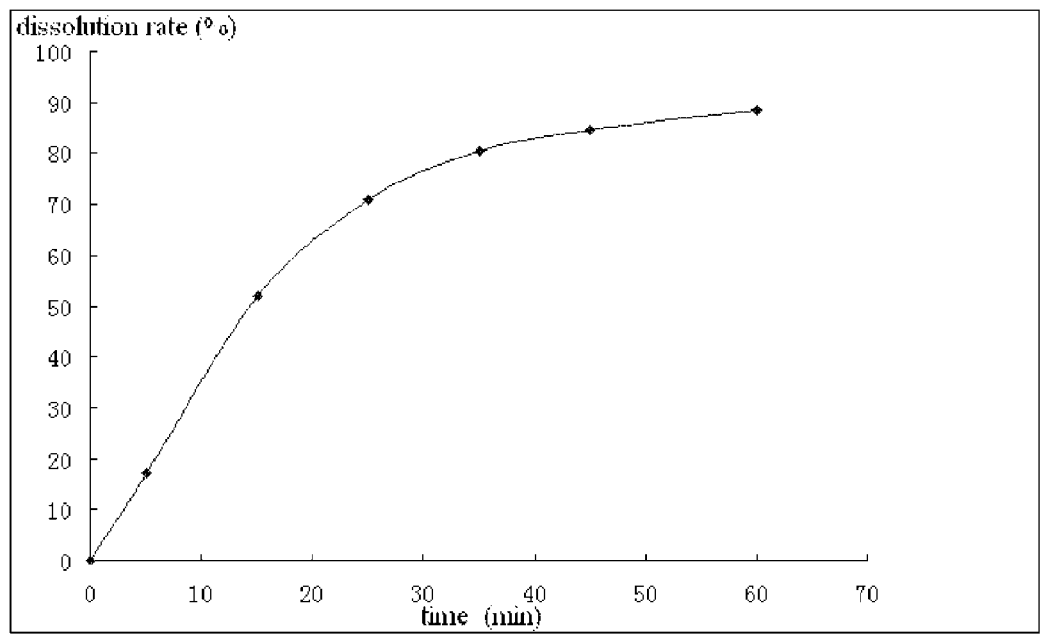
FIG. 1 is an in vitro dissolution curve of a capsule containing total flavonoids of *Desmodium Styracifolium* (example 7) prepared according to an embodiment of the present disclosure.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

Example 1 Preparation of Total Flavonoids Extract of *Desmodium Styracifolium*

200 g raw material of *Desmodium Styracifolium* was weighed, added with 95% ethanol having a weight of 14 times than that of the raw material, followed by heated and refluxed for 3 hours at a temperature of 60° C. for first extraction. The raw material was added with 95% ethanol having a weight of 12 times than that of the raw material, followed by heated and refluxed for 2 hours at a temperature of 50° C. for second extraction. The raw material was added with 80% ethanol having a weight of 8 times than that of the raw material followed by heated and refluxed for 1 hour at a temperature of 50° C. for third extraction. After mixed, resulting alcohol extracting solutions as a whole were concentrated to be of a volume 8 times than the weight of the raw material followed by still standing and filtration, thereby obtaining filtrate (a loading sample) for use. 400 g pharmaceutical-grade AB-8 type macroporous resin, after immersed in an appropriate amount of ethanol, was packed into a column by a wet method, followed by dealt for use.

The filtrate (the loading sample) was subjected to adsorption onto an AB-8 macroporous resin column at a flow rate of 3 column bed volumes per hour, followed by eluted and purified with water having a volume of 12 times than the weight of macroporous resin, and then eluted with 95% ethanol having a volume of 10 column bed volumes at a flow rate of 3 column bed volumes per hour, to obtain an eluted solution. The ethanol was recycled from the eluted solution and the eluted solution was concentrated to a concentrated solution with a relative density of 1.10. 4.03 g extract of *Desmodium Styracifolium* was obtained after dried under reduced pressure at 75° C. and smashed, which was preserved at shady and cool place. After measured by ultraviolet-visible spectrophotometry, the resulting extract of *Desmodium Styracifolium* was of a total flavonoids content of 71.65% (by dried extract, %), and a schaftoside content of 10.30% (by dried extract, %).

Example 2 Preparation of Total Flavonoids Extract of *Desmodium Styracifolium*

200 g raw material of *Desmodium Styracifolium* was weighed, added with 70% ethanol having a weight of 12 times than that of the raw material, followed by heated and refluxed for 2 hours at a temperature of 55° C. for first extraction. The raw material was added with 70% ethanol having a weight of 10 times than that of the raw material, followed by heated and refluxed for 1.5 hours at a temperature of 55° C. for second extraction. After mixed, resulting alcohol extracting solutions as a whole were concentrated to be of a volume 5 times than the weight of the raw material followed by still standing and filtration, thereby obtaining filtrate (a loading sample) for use. 400 g pharmaceutical-grade AB-8 type macroporous resin, after immersed in an appropriate amount of ethanol, was packed into a column by a wet method, followed by dealt for use.

The filtrate (the loading sample) was subjected to adsorption onto an AB-8 macroporous resin column at a flow rate of 1 column bed volume per hour, followed by eluted and purified with water having a volume of 10 times than the weight of macroporous resin, and then eluted with 60% ethanol having a volume of 8 column bed volumes at a flow rate of 2 column bed volumes per hour, to obtain an eluted solution. The ethanol was recycled from the eluted solution and the eluted solution was concentrated to a concentrated solution with a relative density of 1.22. 4.68 g extract of *Desmodium Styracifolium* was obtained after dried under reduced pressure at 75° C. and smashed, which was preserved at shady and cool place. After measured by ultraviolet-visible spectrophotometry, the resulting extract of *Desmodium Styracifolium* was of a total flavonoids content of 63.31% (by dried extract, %), and a schaftoside content of 5.38% (by dried extract, %).

Example 3 Preparation of Total Flavonoids Extract of *Desmodium Styracifolium*

50 kg raw material of *Desmodium Styracifolium* was weighed, added with 80% ethanol having a weight of 12 times than that of the raw material, followed by heated and refluxed for 2 hours at a temperature of 55° C. for first extraction. The raw material was added with 80% ethanol having a weight of 10 times than that of the raw material, followed by heated and refluxed for 1.5 hours at a temperature of 55° C. for second extraction. After mixed, resulting alcohol extracting solutions as a whole were concentrated to be of a volume 5 times than the weight of the raw material followed by still standing and filtration, thereby obtaining filtrate (a loading sample) for use. 100 kg pharmaceutical-grade AB-8 type macroporous resin, after immersed in an appropriate amount of ethanol, was packed into a column by a wet method, followed by dealt for use.

The filtrate (the loading sample) was subjected to adsorption onto an AB-8 macroporous resin column at a flow rate of 2 column bed volumes per hour, followed by eluted and purified with water having a volume of 10 times than the weight of macroporous resin, and then eluted with 60% ethanol having a volume of 8 column bed volumes at a flow rate of 2 column bed volumes per hour, to obtain an eluted solution. The ethanol was recycled from the eluted solution and the eluted solution was concentrated to a concentrated solution with a relative density of 1.22. 1.12 kg extract of *Desmodium Styracifolium* was obtained after dried under reduced pressure at 75° C. and smashed, which was preserved at shady and cool place. After measured by ultraviolet-visible spectrophotometry, the resulting extract of *Desmodium Styracifolium* was of a total flavonoids content of 59.49% (by dried extract, %), and a schaftoside content of 5.10% (by dried extract, %).

Example 4 Preparation of Total Flavonoids Extract of *Desmodium Styracifolium*

50 kg raw material of *Desmodium Styracifolium* was weighed, added with 80% ethanol having a weight of 12 times than that of the raw material, followed by heated and refluxed for 2 hours at a temperature of 55° C. for first extraction. The raw material was added with 80% ethanol having a weight of 10 times than that of the raw material, followed by heated and refluxed for 1.5 hours at a temperature of 55° C. for second extraction. After mixed, resulting alcohol extracting solutions as a whole were concentrated to be of a volume 5 times than the weight of the raw material followed by still standing and filtration, thereby obtaining filtrate (a loading sample) for use. 100 kg pharmaceutical-grade AB-8 type macroporous resin, after immersed in an appropriate amount of ethanol, was packed into a column by a wet method, followed by dealt for use.

The filtrate (the loading sample) was subjected to adsorption onto an AB-8 macroporous resin column at a flow rate of 2 column bed volumes per hour, followed by eluted and purified with water having a volume of 10 times than the weight of macroporous resin, and then eluted with 60% ethanol having a volume of 8 column bed volumes at a flow rate of 2 column bed volumes per hour, to obtain an eluted solution. The ethanol was recycled from the eluted solution and the eluted solution was concentrated to a concentrated solution with a relative density of 1.22. 1.14 kg extract of *Desmodium Styracifolium* was obtained after dried under reduced pressure at 75° C. and smashed, which was preserved at shady and cool place. After measured by ultraviolet-visible spectrophotometry, the resulting extract of *Desmodium Styracifolium* was of a total flavonoids content of 59.37% (by dried extract, %), and a schaftoside content of 5.01% (by dried extract, %).

The above results show that processing parameters used in embodiments of the present disclosure are workable and able to be smoothly transited into industrial production after further adjusted during a pilot test.

Example 5 Preparation of a Capsule Containing Total Flavonoids of *Desmodium Styracifolium*

Formula:

| | |
|---|---|
| total flavonoids of *Desmodium Styracifolium* | 133 g |
| microcrystalline cellulose | 30 g |
| lactose | 37 g |
| povidone $K_{30}$ | 1 g |
| water | 120 g |
| total | 1000 capsules |

Method for Preparing:

a. The total flavonoids extract of *Desmodium Styracifolium* was prepared according to Example 4.

b. 1 g povidone $K_{30}$ was dissolved in 120 g water, thus obtaining a solution of the adhesion agent after stirring, for use.

c. After mixed, 133 g total flavonoids of *Desmodium Styracifolium*, 30 g microcrystalline cellulose, 37 g lactose were added into a fluidized bed, followed by preheated to 45° C. for 20 min. The solution of the adhesion agent was then granulated by spraying, with gunjet under an atomizing pressure of 0.9 bar and a spraying speed of 20 rpm/min, into the fluidized bed (after adjusted with suitable parameters). Such the solution of the adhesion agent was completely sprayed within 15 min, during which a material temperature was held at 45° C. by adjusting air inlet temperature to 55° C.

d. After the granulation, drying was performed by adjusting parameters. In specific, the material temperature was held at 45° C. by adjusting air inlet temperature to 65° C., for 10 min drying.

e. Those granules after dried, were cooled, discharged, and subjected to size stabilization by sieving at 60 meshes, and then capsulized to obtain 1000 capsules containing total flavonoids of *Desmodium Styracifolium*.

Dissolution rate was measured in accordance with the First Method in appendix XC, part II, *Chinese Pharmacopoeia*, 2010 edition.

Testing sample solutions were obtained by the following steps: dissolving the above-obtained capsule in 1000 ml water (as a dissolution medium) contained in a beaker; setting a rotation rate of dissolution rate analysis instruments to be 100 rpm per min; taking 10 ml from the beaker after 5, 15, 25, 35, 45 and 60 min from operations specified in the First Method, followed by filtration; taking 1 ml secondary filtrate precisely each into a 5 ml volumetric flask and adding 0.1 M hydrochloric acid up to graduation on the volumetric flask, followed by shaken to be uniform, thereby obtaining the testing sample solutions.

Reference sample solutions were obtained by the following steps: weighing a certain amount of schaftosides precisely as a reference sample; dissolving the reference sample with an appropriate volume of ethanol in a volumetric flask; adding 0.1 M hydrochloric acid up to graduation on the volumetric flask, thereby obtaining the reference sample solutions each having a schaftoside concentration of 15 µg/ml.

The testing sample solutions and the reference sample solutions were subjected to ultraviolet spectrophotometry (appendix IV A) at 270 nm, for calculating the dissolution rate of each capsule. The dissolution rate curve (as shown in FIG. 1) was plotted by taking time as X-coordinate and accumulative release as Y-coordinate.

Example 6 Preparation of a Capsule Containing Total Flavonoids of *Desmodium Styracifolium*

Formula:

| | |
|---|---|
| total flavonoids of *Desmodium Styracifolium* | 133 g |
| microcrystalline cellulose | 30 g |
| lactose | 37 g |
| povidone $K_{30}$ | 1 g |
| cross-linked sodium carboxymethyl cellulose | 20 g |
| aerosil | 1 g |
| water | 120 g |
| total | 1000 capsules |

Method for Preparing:

a. The total flavonoids extract of *Desmodium Styracifolium* was prepared according to Example 4.

b. The formula dosages of 133 g total flavonoids of *Desmodium Styracifolium*, 30 g microcrystalline cellulose, 37 g lactose, 1 g povidone $K_{30}$, 20 g cross-linked sodium carboxymethyl cellulose were separately sieved at 80 meshes for use. 1 g povidone $K_{30}$ as the adhesion agent was dissolved in 120 g water, thereby obtaining the aqueous solution containing povidone $K_{30}$ after stirred to be uniform for use.

c. The materials in respective formula dosage were preheated to 45° C. for 20 min in a fluidized bed. The solution of the adhesion agent was then granulated by spraying, with gunjet under an atomizing pressure of 0.9 bar and a spraying speed of 20 rpm/min, into the fluidized bed (after adjusted with suitable parameters). Such the solution of the adhesion agent was completely sprayed within 15 min, during which a material temperature was held at 45° C. by adjusting air inlet temperature to 55° C.

d. After the granulation, drying was performed by adjusting parameters. In specific, the material temperature was held at 45° C. by adjusting air inlet temperature to 65° C., for 10 min drying.

e. Those granules after dried, were cooled, discharged, mixed with the cross-linked sodium carboxymethyl cellulose in a mixer, and then subjected to size stabilization by sieving at 60 meshes, after which 1 g aerosil was added and mixed to be uniform, for further capsulization, thereby obtaining 1000 capsules containing total flavonoids of *Desmodium Styracifolium*.

The dissolution rate was measured, same as Example 5, to be 89.9%.

Example 7 Preparation of a Capsule Containing Total Flavonoids of *Desmodium Styracifolium*

Formula:

| | |
|---|---|
| total flavonoids of *Desmodium Styracifolium* | 133 g |
| microcrystalline cellulose | 33 g |
| lactose | 33 g |
| povidone $K_{30}$ | 1 g |
| cross-linked sodium carboxymethyl cellulose | 15 g |
| aerosil | 1 g |
| water | 120 g |
| total | 1000 capsules |

Method for preparing is same as Example 6.

The dissolution rate was measured, same as Example 5, to be 90.5%. Example 8 Preparation of a capsule containing total flavonoids of *Desmodium Styracifolium*

Formula:

| total flavonoids of *Desmodium Styracifolium* | 33 g |
| --- | --- |
| microcrystalline cellulose | 66 g |
| lactose | 66 g |
| povidone K$_{30}$ | 1 g |
| cross-linked sodium carboxymethyl cellulose | 10 g |
| sodium stearyl fumarate | 1 g |
| water | 120 g |
| total | 1000 capsules |

Method for preparing is same as Example 6.

Example 9 Preparation of a Capsule Containing Total Flavonoids of *Desmodium Styracifolium*

Formula:

| total flavonoids of *Desmodium Styracifolium* | 33 g |
| --- | --- |
| microcrystalline cellulose | 33 g |
| lactose | 33 g |
| cross-linked povidone | 60 g |
| polyethylene glycol 6000 | 5 g |
| sodium stearyl fumarate | 5 g |
| water | 120 g |
| total | 1000 capsules |

Method for preparing is same as Example 6.

Example 10 Preparation of a Capsule Containing Total Flavonoids of *Desmodium Styracifolium*

Formula:

| total flavonoids of *Desmodium Styracifolium* | 50 g |
| --- | --- |
| microcrystalline cellulose | 50 g |
| lactose | 50 g |
| polyethylene glycol 6000 | 2 g |
| magnesium stearate | 2 g |
| ethanol | 120 g |
| water | 40 g |
| total | 1000 capsules |

Method for preparing is same as Example 6.

Example 11 Preparation of a Capsule Containing Total Flavonoids of *Desmodium Styracifolium*

Formula:

| total flavonoids of *Desmodium Styracifolium* | 66.5 g |
| --- | --- |
| microcrystalline cellulose | 40 g |
| cross-linked sodium carboxymethyl cellulose | 40 g |
| cross-linked povidone | 30 g |
| polyethylene glycol 6000 | 10 g |
| magnesium stearate | 5 g |
| water | 200 g |
| total | 1000 capsules |

Method for preparing is same as Example 6.
The dissolution rate was measured, same as Example 5, to be 90.0%.

Example 12 Preparation of a Capsule Containing Total Flavonoids of *Desmodium Styracifolium*

Formula:

| total flavonoids of *Desmodium Styracifolium* | 66.5 g |
| --- | --- |
| microcrystalline cellulose | 50 g |
| lactose | 50 g |
| calcium carboxymethyl cellulose | 30 g |
| povidone K$_{30}$ | 2 g |
| magnesium stearate | 5 g |
| water | 180 g |
| total | 1000 capsules |

Method for preparing is same as Example 6.

Example 13 Preparation of a Capsule Containing Total Flavonoids of *Desmodium Styracifolium*

Formula:

| total flavonoids of *Desmodium Styracifolium* | 80 g |
| --- | --- |
| microcrystalline cellulose | 35 g |
| lactose | 30 g |
| povidone K$_{30}$ | 0.1 g |
| magnesium stearate | 5 g |
| water | 80 g |
| total | 1000 capsules |

Method for preparing is same as Example 5.

Example 14 Preparation of a Capsule Containing Total Flavonoids of *Desmodium Styracifolium*

Formula:

| total flavonoids of *Desmodium Styracifolium* | 100 g |
| --- | --- |
| microcrystalline cellulose | 40 g |
| cross-linked sodium carboxymethyl cellulose | 20 g |
| cross-linked povidone | 40 g |
| polyethylene glycol 6000 | 10 g |
| magnesium stearate | 10 g |
| water | 210 g |
| total | 1000 capsules |

Method for preparing is same as Example 6.

Example 15 Preparation of a Capsule Containing Total Flavonoids of *Desmodium Styracifolium*

Formula:

| total flavonoids of *Desmodium Styracifolium* | 100 g |
| --- | --- |
| lactose | 60 g |
| cross-linked sodium carboxymethyl cellulose | 35 g |
| hydroxypropyl methylcellulose | 0.1 g |
| aerosil | 2 g |
| ethanol | 100 g |
| water | 10 g |
| total | 1000 capsules |

Method for preparing is same as Example 6.

Example 16 Preparation of a Capsule Containing Total Flavonoids of *Desmodium Styracifolium*

Formula:

| | |
|---|---|
| total flavonoids of *Desmodium Styracifolium* | 120 g |
| microcrystalline cellulose | 40 g |
| lactose | 40 g |
| povidone $K_{30}$ | 1 g |
| polyethylene glycol 6000 | 1 g |
| aerosil | 2 g |
| ethanol | 96 g |
| water | 24 g |
| total | 1000 capsules |

Method for preparing is same as Example 6.

Example 17 Preparation of a Capsule Containing Total Flavonoids of *Desmodium Styracifolium*

Formula:

| | |
|---|---|
| total flavonoids of *Desmodium Styracifolium* | 120 g |
| hydroxypropyl methylcellulose | 1 g |
| lactose | 120 g |
| povidone $K_{30}$ | 1 g |
| magnesium stearate | 1 g |
| ethanol | 100 g |
| water | 20 g |
| total | 1000 capsules |

Method for preparing is same as Example 6.

Example 18 Preparation of a Capsule Containing Total Flavonoids of *Desmodium Styracifolium*

Formula:

| | |
|---|---|
| total flavonoids of *Desmodium Styracifolium* | 120 g |
| microcrystalline cellulose | 40 g |
| lactose | 40 g |
| polyethylene glycol 6000 | 2 g |
| magnesium stearate | 1 g |
| water | 120 g |
| total | 1000 capsules |

Method for preparing is same as Example 6.

Example 19 Preparation of a Capsule Containing Total Flavonoids of *Desmodium Styracifolium*

Formula:

| | |
|---|---|
| total flavonoids of *Desmodium Styracifolium* | 150 g |
| microcrystalline cellulose | 30 g |
| lactose | 30 g |
| cross-linked povidone | 80 g |
| polyethylene glycol 6000 | 5 g |
| sodium stearyl fumarate | 5 g |
| polyethylene glycol 6000 | 2 g |
| ethanol | 130 g |
| water | 45 g |
| total | 1000 capsules |

Method for preparing is same as Example 6.

Example 20 Preparation of a Capsule Containing Total Flavonoids of *Desmodium Styracifolium*

Formula:

| | |
|---|---|
| total flavonoids of *Desmodium Styracifolium* | 150 g |
| microcrystalline cellulose | 30 g |
| lactose | 20 g |
| povidone $K_{30}$ | 1.2 g |
| aerosil | 2 g |
| water | 80 g |
| total | 1000 capsules |

Method for preparing is same as Example 5.

The dissolution rate was measured, same as Example 5, to be 88.9%.

Example 21 Preparation of a Capsule Containing Total Flavonoids of *Desmodium Styracifolium*

Formula:

| | |
|---|---|
| total flavonoids of *Desmodium Styracifolium* | 200 g |
| microcrystalline cellulose | 30 g |
| lactose | 30 g |
| povidone $K_{30}$ | 2 g |
| aerosil | 2 g |
| water | 120 g |
| total | 1000 capsules |

Method for preparing is same as Example 5.

Example 22 Preparation of a Capsule Containing Total Flavonoids of *Desmodium Styracifolium*

Formula:

| | |
|---|---|
| total flavonoids of *Desmodium Styracifolium* | 400 g |
| microcrystalline cellulose | 50 g |
| lactose | 50 g |
| povidone $K_{30}$ | 2 g |
| aerosil | 4 g |
| water | 200 g |
| total | 1000 capsules |

Method for preparing is same as Example 5.

Example 23 Measurement to the Dissolution Rate of the Capsule Containing Total Flavonoids of *Desmodium Styracifolium*

As for the comparable example, the formula was same as Example 6, and the total flavonoids of *Desmodium Styracifolium* was prepared according to Example 4 with a differences in that the capsule containing total flavonoids of *Desmodium Styracifolium* of Inventive Example was obtained by a fluidized bed granulation process; whilst the capsule containing total flavonoids of *Desmodium Styracifolium* of Comparable Example was obtained by a common wet granulation process.

Formula of Comparable Example:

| | |
|---|---|
| total flavonoids of *Desmodium Styracifolium* | 133 g |
| microcrystalline cellulose | 30 g |
| lactose | 37 g |
| povidone $K_{30}$ | 1 g |

-continued

| | |
|---|---|
| cross-linked sodium carboxymethyl cellulose | 20 g |
| aerosil | 1 g |
| water | 120 g |
| total | 1000 capsules |

Method for Preparing of Comparable Example:

a. The total flavonoids extract of *Desmodium Styracifolium* was prepared in accordance with example 4.

b. The formula dosages of 133 g total flavonoids of *Desmodium Styracifolium*, 30 g microcrystalline cellulose, 37 g lactose, 1 g povidone $K_{30}$, and 20 g cross-linked sodium carboxymethyl cellulose were separately sieved at 80 meshes for use. The povidone $K_{30}$ as the adhesion agent was dissolved in 120 g water, thereby obtaining the aqueous solution containing povidone $K_{30}$ after stirred to be uniform for use.

c. The lactose and the microcrystalline cellulose were mixed to be uniform at first, and then added and mixed with the total flavonoids extract of *Desmodium Styracifolium* to be uniform, followed by added with the aqueous solution containing povidone $K_{30}$. After stirred to be uniform, the resulting mixture was then formed into a soft material, followed by granulation. After dried at 55° C., resulting granules were subjected to size stabilization, and then the microcrystalline cellulose was added thereto. After sieved at 80 meshes, those granules having a particle size between 40 and 80 meshes were added with the aerosil, followed by mixed to be uniform for further capsulization.

Dissolution rate was measured in accordance with the First Method in appendix XC, part II, *Chinese Pharmacopoeia*, 2010 edition, as mentioned in Example 5. The in vitro dissolution rate curve was plotted by taking time as X-coordinate and accumulative release as Y-coordinate.

Figure 2:
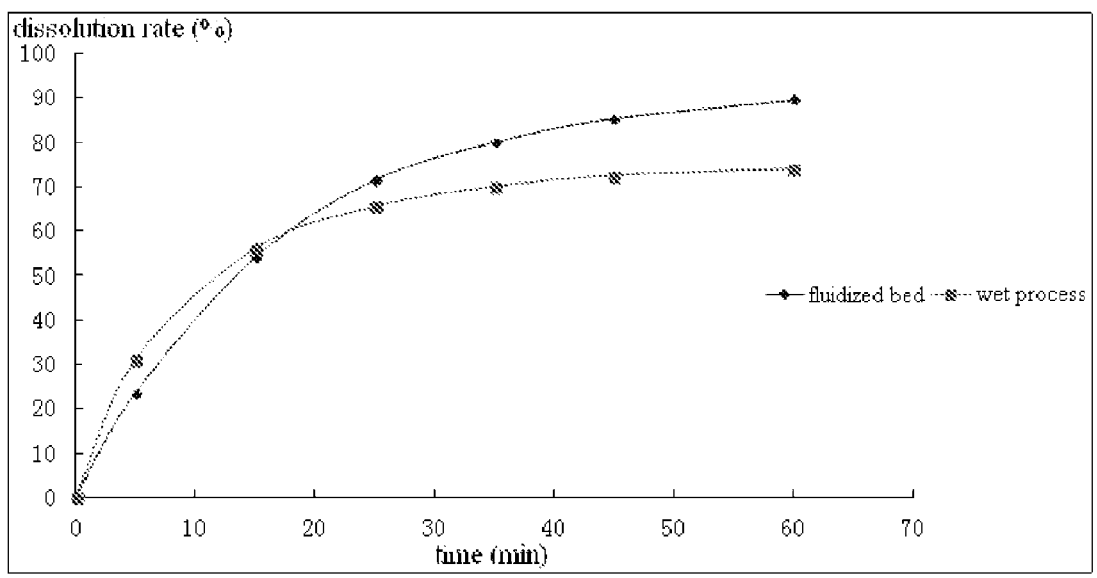
FIG. 2 is a comparison of in vitro dissolution curves of capsules containing total flavonoids of *Desmodium Styracifolium* respectively prepared by a granulation process with fluidized bed and a common wet granulation process (a comparable example) according to an embodiment of the present disclosure.

The dissolution rates of capsules containing total flavonoids of *Desmodium Styracifolium* obtained in the Comparable Example and the Example 6 were measured, and obtaining results of the dissolution rates were shown in Table 1 and the in vitro dissolution rate curve was shown as FIG. 2.

TABLE 1

Dissolution rates of capsules containing total flavonoids of *Desmodium Styracifolium* prepared by two different processes

| Example | Preparation process | Dissolution rate (%) |
|---|---|---|
| Comparable Example | wet granulation | 73.6 |
| Example 6 | fluidized bed granulation | 89.9 |

Example 24 General Pharmacological Experiments of Total Flavonoids of *Desmodium Styracifolium*

Experiment object: to observe the pharmacological effect of total flavonoids of *Desmodium Styracifolium* on general behaviour, state, central nervous system and digestive system of an animal.

Experiment animals and administration: Kunming mice, female, having a weight ranging from 18 g to 22 g, provided by Animal Center of Academy of Military Medical Science with a permit number of experiment animal quality: SOCK (Military) 2002-001, were raised in a mice experiment room of the center with an experiment proved facility number: SYXK (Military) 2002-001.

Experiment grouping: all mice were randomly divided into four groups, i.e., a reference group (administrated with 0.5% sodium carboxymethyl cellulose via gavage), a low-dosage group of total flavonoids of *Desmodium Styracifolium* (75 mg/kg), a middle-dosage group of total flavonoids of *Desmodium Styracifolium* (150 mg/kg) and a high-dosage group of total flavonoids of *Desmodium Styracifolium* (300 mg/kg). Each group contained 10 to 20 mice.

Single gavage was chosen to be the administration route with an administration volume of 0.6 ml/mouse.

Indicators and Results:

1.1 Effects of Total Flavonoids of *Desmodium Styracifolium* on General Behaviour of Mouse The general behaviour of mice was observed according to Bastian classification. Each group contained 10 mice, and the observation started after 15 min from gavage for continuous 60 min, which was performed once again after 24 hours. The observation was made to mental, gait, eye, tail, skin, hair and faeces.

After the observation to the general behaviour of the mice, the total flavonoids of *Desmodium Styracifolium* in the low-, middle- or high-dosage group (75 mg/kg, 150 mg/kg and 300 mg/kg) had little effects on the animal behaviour, action, activity, emotion and gait, with non-significant difference as compared with the reference group.

1.2 Effects of Total Flavonoids of *Desmodium Styracifolium* on Spontaneous Activity The results, recorded by a photoelectric method, showed that the spontaneous activities of the mice administrated with different dosages of total flavonoids of *Desmodium Styracifolium* via gavage had non-significant difference as compared with the reference group, and specific data was shown in Table 2.

TABLE 2

Effect on spontaneous activity of the mice adminitrated with total flavonoids of *Desmodium Styracifolium* via gavage

| animal number | dosage (mg/kg) | before administration (times/3 min) | after administration (times/3 min) | | |
|---|---|---|---|---|---|
| | | | 30 min | 60 min | 120 min |
| 20 | 0 | 43.5 ± 7.2 | 41.8 ± 3.3 | 40.3 ± 3.1 | 37.8 ± 2.2 |
| 20 | 75 | 43.8 ± 5.0 | 41.3 ± 3.1 | 39.8 ± 3.3 | 38.5 ± 1.3 |
| 20 | 150 | 44.8 ± 5.0 | 39.8 ± 2.2 | 39.3 ± 1.7 | 39.5 ± 1.3 |
| 20 | 300 | 43.5 ± 4.2 | 40.5 ± 1.9 | 39.8 ± 2.2 | 39.5 ± 1.9 |

1.3 Effects of Total Flavonoids of *Desmodium Styracifolium* on Activating Central Nervous System of Mice After administrated with total flavonoids of *Desmodium Styracifolium* via gavage, seizure lasting duration of mouse was observed by subjecting ear tips, applied with an appropriate amount of saline and clamped by a fish-mouth clamp at both sides, to electricity stimulation at a voltage of 110 V for 0.3 second.

As can be seen from obtaining result that the seizure lasting duration caused by the electricity stimulation was not significantly prolonged or shortened by total flavonoids of *Desmodium Styracifolium* in the low-, middle- or high-dosage group (75 mg/kg, 150 mg/kg and 300 mg/kg) as compared with the reference group; while the seizure occurrence was not changed significantly either (see the specific data shown in Table 3), thus indicating that the total flavonoids had no obvious activating effect on central nervous system via gavage administration.

TABLE 3

Effects on activating central nervous system of the mice administered with total flavonoids of *Desmodium Styracifolium* via gavage

| animal number | weight (g) | dosage (mg/kg) | seizure lasting duration (sec) |
|---|---|---|---|
| 10 | 21.1 ± 0.6 | 0 | 32.8 ± 5.3 |
| 10 | 20.9 ± 0.8 | 75 | 37.1 ± 8.1 |
| 10 | 20.3 ± 0.7 | 150 | 37.7 ± 6.0 |
| 10 | 21.0 ± 0.9 | 300 | 35.5 ± 8.7 |

1.4 Effects of Total Flavonoids of *Desmodium Styracifolium* on Digestive System of Mice All mice were randomly grouped such that each group contained 10 mice, all of which were fasten for 12 hours before starting experiment. After 1 hour from administration with total flavonoids of *Desmodium Styracifolium*, the experiment mice were administered with a suspending solution made from 5% carbon powder and 10% Arabic gum, with administration volume of 0.2 ml per mouse. All experiment mice were sacrificed after 20 minutes from the administration with the suspending solution for gastrointestinal tract harvest. The gastrointestinal tract was straighten on a glass plate for measuring a distance from pylorus to where the carbon powder headed with a ruler, then a percentage of such the distance to the total length of the gastrointestinal tract was calculated. Obtaining results showed that total flavonoids of *Desmodium Styracifolium* had no obvious effects on gastrointestinal movement. Specific data was shown in Table 4.

TABLE 4

Effects on propelling rate of the mice administered with total flavonoids of *Desmodium Styracifolium* via gavage

| dosage (mg/kg) | total length of gastro-intestinal tract (cm) | distance from pylorus to where the carbon powder headed (cm) | propelling rate (%) |
|---|---|---|---|
| 0 | 52.2 ± 1.9 | 30.2 ± 2.4 | 57.8 ± 4.2 |
| 75 | 52.5 ± 1.7 | 31.6 ± 2.4 | 58.1 ± 3.5 |
| 150 | 52.3 ± 2.3 | 28.8 ± 3.5 | 56.8 ± 5.0 |
| 300 | 52.0 ± 1.9 | 29.8 ± 2.9 | 58.0 ± 3.4 |

Example 25 Pharmacodynamic Experiments of Total Flavonoids of *Desmodium Styracifolium* in Animals 1.1 Experiment of Therapeutic Effects of Total Flavonoids of *Desmodium Styracifolium* on Ethylene Glycol Calcium Oxalate Kidney Stones in Rats As compared with the reference group (administrated with 0.5% sodium carboxymethyl cellulose via gavage), the total flavonoids of *Desmodium Styracifolium* in four dosage groups (50 mg/kg/day, 100 mg/kg/day, 200 mg/kg/day, 400 mg/kg/day) inhibited amount of calcium oxalate crystalline polymer in kidney with a significant dose-effect relationship ($P<0.05$-$0.01$); reduced the formation rate of kidney stones ($P<0.05$-$0.01$); decreased creatinine content ($P<0.05$-$0.01$) and uric acid content ($P<0.05$-$0.01$) in serum, and improved kidney function of rats.

1.2 Experiment of Preventing Effects of Total Flavonoids of *Desmodium Styracifolium* on Ethylene Glycol-Induced Toxic Calcium Oxalate Kidney Stones in Rats As compared with the reference group (administrated with 0.5% sodium carboxymethyl cellulose via gavage), the total flavonoids of *Desmodium Styracifolium* in three dosage groups (50 mg/kg/day, 100 mg/kg/day, 200 mg/kg/day) alleviated pyclectasis, reduced the formation rate of kidney stones, decreased the amount of the calcium oxalate crystalline polymer ($P<0.01$-$0.001$) and decreased the creatinine content and the uric acid content in serum ($P<0.05$-$0.01$).

1.3 Experiment of Dissolving Effect of Total Flavonoids of *Desmodium Styracifolium* on Implanted Human Bladder Stones in Rats As compared with the reference group (administrated with 0.5% sodium carboxymethyl cellulose via gavage), total flavonoids of *Desmodium Styracifolium* in three dosage groups (100 mg/kg/day, 200 mg/kg/day, 400 mg/kg/day) had effects of dissolving stones and reducing the formation of new stones. The total flavonoids of *Desmodium Styracifolium* in 100 mg/kg/day group lightened the stone weight ($P<0.05$). The total flavonoids of *Desmodium Styracifolium* in 200 gm/kg/day group lightened the stone weight ($P<0.05$) and dissolved 20% stones. The total flavonoids of *Desmodium Styracifolium* in 400 gm/kg/day group lightened the stone weigh ($P<0.01$) and dissolved 30% stones.

1.4 Experiment of Diuretic Effects of Total Flavonoids of *Desmodium Styracifolium* on Rats Suffering Ethylene Glycol-Induced Kidney Stones and Normal Rats As compared with a model group, rats in three dosage groups (50 mg/kg/day, 100 mg/kg/day, 200 mg/kg/day) had a total urine output ranging from 76.4 to 89.5 ml, which was 29-36 ml more than that of rats in the normal group (48.1 ml) after 6 hours from single administration. After 4 weeks treatment with administration to those rats suffering stones, the urine output within 12 hours was increased significantly, 12-36% more than that in the model group.

1.5 Experiment of Inhibition Effects of Total Flavonoids of *Desmodium Styracifolium* on Swelling Degree and Rate Swelling in Rat Toe Injected with Fresh Albumen As compared with the reference group (administrated with 0.5% sodium carboxymethyl cellulose via gavage), total flavonoids of *Desmodium Styracifolium* in three dosage groups (100 mg/kg/day, 200 mg/kg/day, 400 mg/kg/day) alleviated the swelling degree and the rate swelling in rat toe injected with fresh albumen, indicating that total flavonoids of *Desmodium Styracifolium* has a certain anti-inflammatory effect and has an obvious inhibiting effect on proliferation of granulation tissue.

Example 26 Acute Toxicity Test of Total Flavonoids of *Desmodium Styracifolium* in Animals 1.1 Acute Toxicity Tests of Total Flavonoids of *Desmodium Styracifolium* in Mice All mice were randomly divided into 6 groups, each containing 20 mice with 10 male and 10 female, with 0.85 distances between groups. After administration, decreased activities, unstable gait, weakened breaths appeared in animals. Most mice died within an hour after the administration, and a few of mice died within 1 to 6 hours after the administration. After calculation by Bliss, LD50 for female was 18.162 g/kg with an upper limit of 20.199 g/kg and a lower limit of 16.326 g/kg under a confidence limit of 95%; LD50 for male was 17.084 g/kg with an upper limit of 18.975 g/kg and a lower limit of 15.301 g/kg under a confidence limit of 95%, with no obvious difference as for LD50 between female and male. According to the results described above, total flavonoids of *Desmodium Styracifolium* could be recognized as a substantially nontoxic medicament.

1.2 Acute Toxicity Tests of Total Flavonoids of *Desmodium Styracifolium* in Rats The test was performed according to "fixed dosage by single oral administration". Rats were administrated with 2000 mg/kg total flavonoids of *Desmodium Styracifolium* for preliminary tests, resulting in nonobvious acute toxic reaction; accordingly, 2000 mg/kg was taken as the fixed dosage for formal tests.

Rats for the test were randomly divided into a reference group and an administration group, each containing 10 animals with 5 female and 5 male. Rats in the administration group were administrated with 2000 mg/kg total flavonoids of *Desmodium Styracifolium* by single gavage, with an administration volume of 2.0 ml/100 g body weight. Rats in the reference group were administrated with 0.5% sodium carboxymethyl cellulose by single gavage, with an administration volume of 2.0 ml/100 g body weight.

Rats in the administration group became lazy to move within 3 hours from the administration; excreted faeces in an ash black color after 1 day from the administration; consumed slightly reduced amount of food, had mildly inhibited increasement in body weight, which recovered to those in the reference group. According to the results described above, total flavonoids of *Desmodium Styracifolium* could be regarded as a tested medicament without severe and acute toxicity.

Example 27 Long Term Toxicity Tests of Total Flavonoids of *Desmodium Styracifolium* in Animals 1.1 Long Term Toxicity Tests in Rats Administrated with Total Flavonoids of *Desmodium Styracifolium* by Gavage Three dosage groups were designed to be a low dosage group of 200 mg/kg/day, a middle dosage group of 600 mg/kg/day, a high dosage group 1800 mg/kg/day, which were equivalent to 11.7, 35.1 and 105.3 times of the dosage for human respectively, along with a reference group in which rats were administrated with 0.5% sodium carboxymethyl cellulose. The rats were administrated 6 times per week for 26 continuous weeks by gavage. Rats were observed in terms of general drug reaction, biochemical indicators in urine, visible components in peripheral blood, clotting time, biochemical indicators in serum, organ weight, and histopathology.

All rats in every group were survived until predetermined sacrificing time. Rats in the reference group, the low dosage group and the middle dosage group behaved lively, had soft and polish hair, excreted faeces in a granule shape. A few rats in the high dosage group were in a slight emaciation shape with slightly yellow and unruly hair after 14 to 26 weeks from the administration. During 26 weeks after the administration, increasements of body weights were mildly inhibited by the high dosage group after 15 to 26 weeks from the administration for female and after 21 weeks from the administration to 2 weeks subsequent to administration withdraw for male, without statistical difference as compared with the reference group. Increasements of body weights in the high dosage group recovered to that in the reference group after 4 weeks after administration withdraw. Male rats in the high dosage group exhibited an aspartate aminotransferase level obviously higher than that in the reference group ($P<0.05$) after 26 weeks from the administration. Male and female rats in the middle dosage group all exhibited a total serum bilirubin content significantly lower than that in the reference group ($P<0.05$) after 13 weeks from the administration. Male rats in the high dosage group exhibited a total cholesterol content in serum obviously lower than that in the reference group ($P<0.01$) after 26 weeks from the administration. Rats in the middle dosage group still exhibited the total cholesterol content in serum obviously lower than that in the reference group after 4 weeks from the administration withdraw. All these changes could be related to the pharmacological effect of total flavonoids of *Desmodium Styracifolium*. Other indicators had no significant difference among groups. After 4 weeks from the administration withdraw, all of indicated mentioned above which had been changed recovered to that in the reference group.

According to histological examination, no pathological alteration related to the administration of total flavonoids of *Desmodium Styracifolium* has been found in each group with different dosages.

1.2 Long Term Toxicity Tests in Beagles Administrated with Total Flavonoids of *Desmodium Styracifolium* by Gavage Three dosage groups were designed to be a low dosage group of 100 mg/kg/day, a middle dosage group of 300 mg/kg/day, a high dosage group 900 mg/kg/day, along with a reference group in which beagles were administrated with 0.5% sodium carboxymethyl cellulose, there were 6 beagles in each group. Beagles having normal state were selected to be subjected to various of indexes two or three times, and the beagles were subsequently selected to be evenly and randomly divided into groups, each containing 3 male and 3 female.

All beagles were survived until predetermined time. During the test, beagles in each group had polish hair, good appetite and a normal temperature. A few beagles in the high dosage group were in a slight poor appetite after 4.5 to 6.0 months from the administration. After 1 month from the administration withdraw, all of indicated mentioned above which had been changed recovered to that in the reference group. During the administration, increasements of body weights were obviously inhibited by the high dosage group during the administration, and after 6.0 months from the administration, there was an obvious difference compared with the reference group after 6 months from the administration. After 1 month from the administration withdraw, all of indicated mentioned above which had been changed recovered to that in the reference group. Beagles in the high dosage group exhibited an aspartate aminotransferase level and an urea nitrogen level obviously higher than those in the reference group after 6.0 months from the administration. During the administration, beagle in each group all exhibited improved total serum bilirubin level and total cholesterol level. After 1 month from the administration withdraw, all of indicated mentioned above had been changed recovered to normal.

According to histological examination, no pathological alteration related to the administration of total flavonoids of *Desmodium Styracifolium* has been found in each group with different dosages.

Example 28 random, double-blind, multi-dosage parallel-controlled and multi-centered II phase clinical trial about effectivity and safety of the capsule containing total flavonoids of *Desmodium Styracifolium* for treating urinary stone (stagnation of dampness-heat)

Approval Document of Medicament Clinical Trial: 2007L04844 inclusion criteria of the clinical trial: (1) renal pelvic stones and ureteral stones; (2) having an age ranging from 18 to 65 years old; (3) 0.4 cm<stone diameter≤1.0 cm; (4) good kidney function, in particularly in a kidney suffering from the stones (if the patient has hydronephrosis, it should be less than moderate level); (5) a good body condition with life-independent ability; (6) well-known about the study and a consent to sign the paper.

exclusion criteria of the clinical trial: (1) malformation, stenosis, obstruction and surgery scar synechia are present at a connection portion between the kidney and the ureter or at distal ureter; (2) severe hydronephrosis (type III); (3) continuous severe hematuria or even shock; (4) acute obstruction oliguria or anuria; (5) pregnancy or lactation female; (6) heart and cerebral vessels, liver, kidney and hemopoietic system-combined severe idiopathic diseases, or fatal diseases endangering life (such as tumor or AIDs), or mentally or legally disabled patient; (7) having liver function ALT and/or AST value beyond a normal range; (8) urolithiasis patient intervened with surgery treatment in the past month; (9) other diseases with reduced possibilities of assignment or complicating assignment determined by researcher, such as loss to follow-up caused by job changing; (10) participant in other clinical trials in last three months; (11) allergy to the medicament or ingredients therein.

Tests were performed in random, double-blind, multi-dosage parallel-controlled and multi-centered ways.

A group (high dosage group): the capsule containing total flavonoids of *Desmodium Styracifolium*×5

B group (middle dosage group): the capsule containing total flavonoids of *Desmodium Styracifolium*×3+capsule containing a simulant agent×2

C group (low dosage group): capsule containing a simulant agent×5

Subjects: patients diagnosed with renal pelvic stones or ureteral stones, fitted in the pattern of dampness-heat brewing and binding, 18 to 65 years old, willing to sign a consent paper.

Administration scheme: 5 capsules containing the simulant agent/3 capsules containing total flavonoids of *Desmodium* Styracifolium+2 capsules containing the simulant agent/5 capsules containing total flavonoids of *Desmodium Styracifolium* were taken orally each time and three times one day (the capsule containing total flavonoids of *Desmodium Styracifolium* and the capsule containing the simulant agent each are of a quality of 0.02 g/capsule. Each capsule containing total flavonoids of *Desmodium Styracifolium* is of a total flavonoids content of 133 mg. Each capsule containing the simulant agent is of a total flavonoids content of 1.33 mg). The administration period is 4 weeks.

The indicators for evaluating effectivity include: (1) X-ray examination (KUB, IVP, Ctu/Mru/CT); (2) single examination: symptoms and signs; (3) symptoms integrals.

The indicators for evaluating safety include: (1) physical examination: body temperature, breath, heartbeat and resting blood pressure; (2) blood routine examination, urine routine examination, liver function (ALT, AST, Tbil, ALP, γ-GT), kidney function (Cr, Bun), coagulation tests, total cholesterol; (3) electrocardiogram; (4) adverse event.

All statistical tests were two-sided, P value was smaller than or equal to a standard with a statistical significance (unless specified).

Statistical Analysis Population:

Full Analysis Set (FAS): refers to a set of ideal subjects having a trend to intentional analysis principle Per Protocol Set (PPS): all the files accorded with experimental treatment, a good compliance, amount of tested medicament between 80% and 120% and a completely filled content by CRF standard, the major variable may be measured, the baseline variable has no deficiency and there is no large contrary to the experimental design.

Safety Analysis Set (SS): the subject at least treated once after randomization.

The full analysis set and the per protocol set were selected by the analyses of the major variable and the comprehensive curative effect, respectively. The full analysis set was selected by demography and other baseline variable and the per protocol set was selected by other analyses of curative effect indexes. The safety analysis set was selected by a safety index analysis.

The test has 68 patients, and there are 22 patients, 24 patients and 22 patients in the large dosage group, the middle dosage group and the small dosage group. The FAS includes 22 from the large dosage group, 23 from the middle dosage group and 22 from the small dosage group. The PPS includes 20 from the large dosage group, 22 from the middle dosage group and 22 from the small dosage group. The SS includes 22 from the large dosage group, 23 from the middle dosage group and 22 from the small dosage group. Two from the large dosage group and two from the middle dosage group were taken off, and one from the middle dosage was eliminated. The difference of elimination rates among three groups had no statistical significance (P=0.3652). Three from the large dosage group and two from the middle dosage group had poor compliances and the difference of occurrence rates of poor compliance among three groups had no statistical significance (P=0.2220). The distributions of demography characteristic, vital signs and accompanied diseases of the patients of three groups were similar and the difference had no statistical significance. The differences of stone conditions at the baselines of three groups and primary symptom of traditional Chinese symptom classification both had no statistical significance.

1. Primary Curative Effect: Effective Rate of Discharging Stones

Result of the FAS: the effective rate of discharging stones of the large dosage group was 63.64%, the effective rate of discharging stones of the middle dosage group was 69.57%, and the effective rate of discharging stones of the small dosage group was 50.00%. Analyzed by a logistic regression of the control center effect, the difference between the large dosage group and the middle dosage group had no statistical significance (P=0.6857), the difference between the large dosage group and the small dosage group had no statistical significance (P=0.3476), the difference between the middle dosage group and the small dosage group had no statistical significance (P=0.1806).

Result of the PPS: the effective rate of discharging stones of the large dosage group was 70%, the effective rate of discharging stones of the middle dosage group was 72.73%, and the effective rate of discharging stones of the small dosage group was 50.00%. Analyzed by a logistic regression of the control center effect, the difference between the large dosage group and the middle dosage group had no statistical significance (P=0.9168), the difference between the large dosage group and the small dosage group had no statistical significance (P=0.1764), the difference between the middle dosage group and the small dosage group had no statistical significance (P=0.1366).

2. Secondary Curative Effect 2.1 Discharging Time

Result of the FAS: after 14 and 28 days from the treatment, the discharging rates of the large dosage group were 35.00% and 35.00%, respectively, the discharging rates of the middle dosage group were 43.48% and 26.09%, respectively, and the discharging rates of the small dosage group were 36.36% and 13.64%, respectively. Analyzed by $CMH_\chi^2$ test, the difference among the discharging time of three groups had no statistical significance (P=0.4489).

2.2 Traditional Chinese Medicine Syndrome

Result of the FAS: effective rates of three groups were 85% of the large dosage group, 95.65% of middle dosage group and 77.27% of small dosage group. Analyzed by a Kruskal-Wallis test, the difference among three groups had no statistical significance (P=0.5841).

Result of the random, double-blind, multi-dosage parallel-controlled and multi-centered II phase clinical trial about efficacy and safety of capsule containing total flavonoids of *Desmodium Styracifolium* for treating urinary stone (stagnation of dampness-heat) shows that the effective rate of treating urinary stone (stagnation of dampness-heat) with the capsule containing total flavonoids of *Desmodium Styracifolium* is 95.65% (each capsule includes 133 mg of the total flavonoids extract of *Desmodium Styracifolium*, orally taken for 3 times per day, 3 capsules for each time, administrated for 4 weeks).

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A capsule, comprising
total flavonoids of *Desmodium Styracifolium*, as an active ingredient, provided in a form of alcohol extract of *Desmodium Styracifolium*, and
a pharmaceutically acceptable excipient,
wherein the pharmaceutically acceptable excipient comprises a filling agent, an adhesion agent, a wetting agent, a disintegrating agent and a lubricating agent, and
the alcohol extract of *Desmodium Styracifolium* is obtained by the following steps:
heating and refluxing a raw material of *Desmodium Styracifolium* with ethanol, so as to obtain an extracting solution of *Desmodium Styracifolium*, the ethanol being of a concentration ranging from 50% to 95% and a weight ranging from 8 to 14 times than that of the raw material of *Desmodium styracifolium*;
concentrating the extracting solution of *Desmodium Styracifolium*, so as to remove ethanol; and
subjecting the extracting solution of *Desmodium Styracifolium* after concentrated to adsorption onto a macroporous resin column, so as to obtain the alcohol extract of *Desmodium Styracifolium*.

2. The capsule according to claim 1, wherein the extracting solution of *Desmodium Styracifolium* is obtained by:
heating and refluxing the raw material of *Desmodium Styracifolium*, for 1 to 3 times with 1 to 3 hours for each time, with ethanol having the concentration ranging from 50% to 95% and the weight ranging from 8 to 14 times than that of *Desmodium Styracifolium* for extraction, and
mixing the ethanol extracting solutions.

3. The capsule according to claim 1, wherein the filling agent is at least one selected from corn starch, dextrin, lactose, pregelatinized starch, saccharose, microcrystalline cellulose, mannitol, sorbitol, xylitol, calcium hydrophosphate and calcium carbonate.

4. The capsule according to claim 1, wherein the adhesion agent is at least one selected from starch paste, hydroxypropyl methylcellulose, povidone $K_{30}$, povidone $K_{25}$, polyethylene glycol 6000, methylcellulose and ethanol.

5. The capsule according to claim 1, wherein the wetting agent is at least one selected from water and ethanol.

6. The capsule according to claim 1, wherein the disintegrating agent is at least one selected from sodium carboxymethyl starch, low-substituted hydroxypropyl cellulose, cross-linked povidone, dry starch, cross-linked sodium carboxymethyl cellulose and calcium carboxymethyl cellulose.

7. The capsule according to claim 1, wherein the lubricating agent is at least one selected from magnesium stearate, talc, aerosol, magnesium dodecyl sulfate, sodium dodecyl sulfate, sodium benzoate and sodium stearyl fumarate.

8. The capsule according to claim 1, comprising
33 to 400 weight parts of the total flavonoids of *Desmodium Styracifolium*,
30 to 120 weight parts of the filling agent,
0.1 to 10 weight parts of the adhesion agent,
1 to 80 weight parts of the disintegrating agent,
1 to 10 weight parts of the lubricating agent, and
80 to 210 weight parts of the wetting agent.

9. The capsule according to claim 8, comprising
33 weight parts of the total flavonoids of *Desmodium Styracifolium*,
66 weight parts of microcrystalline cellulose,
66 weight parts of lactose,
1 weight part of povidone $K_{30}$,
10 weight parts of cross-linked sodium carboxymethyl cellulose,
1 weight part of sodium stearyl fumarate, and
120 weight parts of water; or
33 weight parts of the total flavonoids of *Desmodium Styracifolium*,
33 weight parts of microcrystalline cellulose,
33 weight parts of lactose,
60 weight parts of cross-linked povidone,
5 weight parts of polyethylene glycol 6000,
5 weight parts of sodium stearyl fumarate, and
120 weight parts of water; or
50 weight parts of the total flavonoids of *Desmodium Styracifolium*,
50 weight parts of microcrystalline cellulose,
50 weight parts of lactose,
2 weight parts of polyethylene glycol 6000,
2 weight parts of magnesium stearate,
120 weight parts of ethanol, and
40 weight parts of water; or
66.5 weight parts of the total flavonoids of *Desmodium Styracifolium*,
40 weight parts of microcrystalline cellulose,
40 weight parts of cross-linked sodium carboxymethyl cellulose, 30 weight parts of cross-linked povidone,
10 weight parts of polyethylene glycol 6000,
5 weight parts of magnesium stearate, and
200 weight parts of water; or
66.5 weight parts of the total flavonoids of *Desmodium Styracifolium*,
50 weight parts of microcrystalline cellulose,
50 weight parts of lactose,
30 weight parts of calcium carboxymethyl cellulose,
2 weight parts of povidone $K_{30}$,
5 weight parts of magnesium stearate, and
180 weight parts of water; or
80 weight parts of the total flavonoids of *Desmodium Styracifolium*,
35 weight parts of microcrystalline cellulose,
30 weight parts of lactose,
0.1 weight parts of povidone $K_{30}$,
5 weight parts of magnesium stearate, and
80 weight parts of water; or
100 weight parts of the total flavonoids of *Desmodium Styracifolium*,
60 weight parts of lactose,
35 weight parts of cross-linked sodium carboxymethyl cellulose,
0.1 weight parts of hydroxypropyl methylcellulose,
2 weight parts of aerosol,
100 weight parts of ethanol, and
10 weight parts of water; or
100 weight parts of the total flavonoids of *Desmodium Styracifolium*,
40 weight parts of microcrystalline cellulose,
20 weight parts of cross-linked sodium carboxymethyl cellulose,
40 weight parts of cross-linked povidone,
10 weight parts of polyethylene glycol 6000,
10 weight parts of magnesium stearate, and
210 weight parts of water; or
120 weight parts of the total flavonoids of *Desmodium Styracifolium*,
40 weight parts of microcrystalline cellulose,
40 weight parts of lactose,
2 weight parts of polyethylene glycol 6000,
2 weight parts of magnesium stearate, and
120 weight parts of water; or
120 weight parts of the total flavonoids of *Desmodium Styracifolium*,
120 weight parts of lactose,
1 weight part of hydroxypropyl methylcellulose,
1 weight part of magnesium stearate,
100 weight parts of ethanol, and
20 weight parts of water; or
120 weight parts of the total flavonoids of *Desmodium Styracifolium*,
40 weight parts of microcrystalline cellulose,
40 weight parts of lactose,
1 weight part of polyethylene glycol 6000,
1 weight part of povidone $K_{30}$,
2 weight parts of aerosol,
96 weight parts of ethanol, and
24 weight parts of water; or
133 weight parts of the total flavonoids of *Desmodium Styracifolium*,
30 weight parts of microcrystalline cellulose,
37 weight parts of lactose,
1 weight part of povidone $K_{30}$, and
120 weight parts of water; or
133 weight parts of the total flavonoids of *Desmodium Styracifolium*,
30 weight parts of microcrystalline cellulose,
37 weight parts of lactose,
1 weight part of povidone $K_{30}$,
20 weight parts of cross-linked sodium carboxymethyl cellulose,
1 weight part of aerosol, and
120 weight parts of water; or
133 weight parts of the total flavonoids of *Desmodium Styracifolium*,
33 weight parts of microcrystalline cellulose,
33 weight parts of lactose,
1 weight part of povidone $K_{30}$,
15 weight parts of cross-linked sodium carboxymethyl cellulose,
1 weight part of aerosol, and
120 weight parts of water; or
150 weight parts of the total flavonoids of *Desmodium Styracifolium*,
30 weight parts of microcrystalline cellulose,
30 weight parts of lactose,
80 weight parts of cross-linked povidone,
5 weight parts of polyethylene glycol 6000,
5 weight parts of sodium stearyl fumarate,
130 weight parts of ethanol, and
45 weight parts of water; or
150 weight parts of the total flavonoids of *Desmodium Styracifolium*,
30 weight parts of microcrystalline cellulose,
20 weight parts of lactose,
1.2 weight parts of povidone $K_{30}$,
2 weight parts of aerosol, and
80 weight parts of water; or
200 weight parts of the total flavonoids of *Desmodium Styracifolium*,
30 weight parts of microcrystalline cellulose,
30 weight parts of lactose,
2 weight parts of povidone $K_{30}$,
2 weight parts of aerosol, and
120 weight parts of water; or
400 weight parts of the total flavonoids of *Desmodium Styracifolium*,
50 weight parts of microcrystalline cellulose,
50 weight parts of lactose,
2 weight parts of povidone $K_{30}$,
4 weight parts of aerosol, and
200 weight parts of water.

* * * * *